United States Patent
Baker et al.

(10) Patent No.: US 10,086,041 B2
(45) Date of Patent: Oct. 2, 2018

(54) SYNDECAN-4 PROTEOLIPOSOMES FOR ENHANCED CUTANEOUS WOUND HEALING AND MINIMIZED INFLAMMATORY IMMUNE RESPONSE

(71) Applicant: Board of Regents, The University of Texas System, Austin, TX (US)

(72) Inventors: Aaron B. Baker, Austin, TX (US); Subhamoy Das, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/387,201

(22) Filed: Dec. 21, 2016

(65) Prior Publication Data
US 2017/0189479 A1 Jul. 6, 2017

Related U.S. Application Data

(60) Provisional application No. 62/274,501, filed on Jan. 4, 2016.

(51) Int. Cl.
| | | |
|---|---|---|
| *A61K 38/17* | (2006.01) | |
| *A61K 38/18* | (2006.01) | |
| *A61K 9/50* | (2006.01) | |
| *A61K 9/48* | (2006.01) | |
| *A61P 17/02* | (2006.01) | |
| *A61K 9/127* | (2006.01) | |
| *A61K 9/00* | (2006.01) | |

(52) U.S. Cl.
CPC ............ *A61K 38/177* (2013.01); *A61K 9/127* (2013.01); *A61K 38/179* (2013.01); *A61K 38/1858* (2013.01); *A61K 9/0014* (2013.01); *A61K 9/1277* (2013.01)

(58) Field of Classification Search
CPC ................ A61K 9/0014; A61K 38/177; A61K 38/1858; A61K 38/179; A61K 9/127; A61K 9/1277
See application file for complete search history.

(56) References Cited

U.S. PATENT DOCUMENTS

| | | | |
|---|---|---|---|
| 6,001,805 A * | 12/1999 | Jaynes .................. | A61K 38/10 435/1.1 |
| 2002/0150564 A1 | 10/2002 | Ensley et al. | |
| 2008/0127290 A1 | 5/2008 | Delegue et al. | |
| 2009/0220588 A1 * | 9/2009 | Edelman ................ | A61K 38/39 424/450 |
| 2010/0080788 A1 | 4/2010 | Barnett et al. | |
| 2012/0207819 A1 | 8/2012 | Galili et al. | |
| 2015/0343068 A1 | 12/2015 | Baker et al. | |

OTHER PUBLICATIONS

Hunt et al, An alginate hydrogel matrix for the localised delivery of a fibroblast/keratinocyte co-culture, Biotechnol. J., 2009, 4, pp. 730-737.*

Dobra et al, Growth Factors Regulate the Expression Profile of their Syndecan Co-receptors and the Differentiation of Mesothelioma Cells, Anticancer Research, 2003, 23, pp. 2435-2444.*

Acosta, et al. , "Epidermal growth factor intralesional infiltrations can prevent amputation in patients with advanced diabetic foot wounds.", Int Wound J. 3(3), 2006, 232-9.

Araki, et al. ,"Clustering of syndecan-4 and integrin beta1 by laminin alpha 3 chain—derived peptide promotes keratinocyte migration", Molecular biology of the cell 20, 2009, 3012-3024.

Baker, et al., "Heparanase alters arterial structure, mechanics, and repair following endovascular stenting in mice", Circulation research 104, 2009, 380-387.

Baker, et al., "Heparanase regulates thrombosis in vascular injury and stent-induced flow disturbance.", Journal of the American College of Cardiology 59, 2012, 1551-1560.

Baker, et al., "Regulation of heparanase expression in coronary artery disease in diabetic, hyperlipidemic swine", Atherosclerosis 213, 436-442, doi:10.1016/j.atherosclerosis.2010.09.003 (2010)., 436-442.

Barbul, et al., "Interleukin 2 enhances wound healing in rats.", The Journal of surgical research 40, 1986, 315-319.

Bass, et al., "A syndecan-4 hair trigger initiates wound healing through caveolin- and RhoG-regulated integrin endocytosis.", Developmental cell 21, 2011, 681-693.

Bhansali, et al., "Which is the better option: recombinant human PDGF-BB 0.01% gel or standard wound care, in diabetic neuropathic large plantar ulcers off-loaded by a customized contact cast?", Diabetes research and clinical practice 83, 2009, e13-e16.

Boyanovsky, et al., "Syndecan-4 mediates macrophage uptake of group V secretory phospholipase A2-modified LDL.", Journal of lipid research 50, 2009, 641-650.

Brancato, et al., "Wound macrophages as key regulators of repair: origin, phenotype, and function.", The American journal of pathology 178, 2011, 19-25.

Branski, et al., "Gene therapy in wound healing: present status and future directions", Gene therapy 14, 2007, 1-10.

Brooks, et al., "Syndecan-4 independently regulates multiple small GTPases to promote fibroblast migration during wound healing.", Small GTPases 3, 2012, 73-79.

Brubaker, et al., "An improved cell isolation method for flow cytometric and functional analyses of cutaneous wound leukocytes.", J Immunol Methods 373, 2011, 161-166.

Bruhn-Olszewska "Molecular factors involved in the development of diabetic foot syndrome", Acta biochimica Polonica 59, 2012, 507-513.

Brule, et al., "The shedding of syndecan-4 and syndecan-1 from HeLa cells and human primary macrophages is accelerated by SDF-1/CXCL12 and mediated by the matrix metalloproteinase-9", Glycobiology 16, 2006, 488-501.

(Continued)

*Primary Examiner* — Julie Ha
*Assistant Examiner* — Li N Komatsu
(74) *Attorney, Agent, or Firm* — Meunier Carlin & Curfman LLC

(57) ABSTRACT

Disclosed herein are compositions and articles for wound healing that contain proteovesicles, comprising a syndecan polypeptide embedded in a lipid vesicle, and a PDGF polypeptide. Also disclosed is the use of these compositions to enhance wound healing.

15 Claims, 16 Drawing Sheets

(56) References Cited

OTHER PUBLICATIONS

Buchberger, et al., "The evidence for the use of growth factors and active skin substitutes for the treatment of non-infected diabetic foot ulcers (DFU): a health technology assessment (HTA)", Exp Clin Endocrinol Diabetes. 119(8), 2011, 472-479.

Daley, et al., "The phenotype of murine wound macrophages", Journal of leukocyte biology 87, 2010, 59-67.

Das, et al., "Overcoming disease-induced growth factor resistance in therapeutic angiogenesis using recombinant co-receptors delivered by a liposomal system", Biomaterials 35, 2014, 196-205.

Echtermeyer, et al., "Delayed wound repair and impaired angiogenesis in mice lacking syndecan-4.", The Journal of clinical investigation 107, 2001, R9-R14.

Fang, et al., "A review of becaplermin gel in the treatment of diabetic neuropathic foot ulcers.", Biologics : targets & therapy 2, 2008, 1-12.

Fernandez-Montequin, et al., "Intralesional administration of epidermal growth factor-based formulation (Heberprot-P) in chronic diabetic foot ulcer: treatment up to complete wound closure", Int Wound J. 6(1), 2009, 67-72.

Fiddes, et al., "Preclinical wound-healing studies with recombinant human basic fibroblast growth factor", Annals of the New York Academy of Sciences 638, 1991, 316-328.

Gallo, et al., "Syndecans-1 and -4 are induced during wound repair of neonatal but not fetal skin.", The Journal of investigative dermatology 107, 1996, 676-683.

Goldman, et al., "Growth factors and chronic wound healing: past, present, and future", Advances in skin & wound care 17, 2004, 24-35.

Hebda, et al., "Basic fibroblast growth factor stimulation of epidermal wound healing in pigs", The Journal of investigative dermatology 95, 1990, 626-631.

Hirose, et al., "The local injection of peritoneal macrophages induces neovascularization in rat ischemic hind limb muscles.", Cell transplantation 17, 2008, 211-222.

Hong, et al., "The effect of various concentrations of human recombinant epidermal growth factor on split-thickness skin wounds.", International wound journal 3,, 2006, 123-130.

Ishiguro, et al., "Syndecan-4 as a molecule involved in defense mechanisms.", Glycoconjugate journal 19, 315-318, 2002, 315-318.

Jang, et al., "Syndecan-4 proteoliposomes enhance fibroblast growth factor-2 (FGF-2)-induced proliferation, migration, and neovascularization of ischemic muscle.", Proceedings of the National Academy of Sciences of the United States of America 109, 2012, 1679-1684.

Larsson, et al., "Long-term prognosis after healed amputation in patients with diabetes", Clinical orthopaedics and related research, 1998, 149-158.

Lin, et al., "Essential involvement of IL-6 in the skin wound-healing process as evidenced by delayed wound healing in IL-6-deficient mice", Journal of leukocyte biology 73, 2003, 713-721.

Lin, et al., "Three-dimensional migration of human adult dermal fibroblasts from collagen lattices into fibrin/fibronectin gels requires syndecan-4 proteoglycan", The Journal of investigative dermatology 124, 2005, 906-913.

Lynch, et al., "Growth factors in wound healing. Single and synergistic effects on partial thickness porcine skin wounds", The Journal of clinical investigation 84, doi:10.1172/JCI114210, 1989, 640-646.

Manon-Jensen, et al., "Mapping of matrix metalloproteinase cleavage sites on syndecan-1 and syndecan-4 ectodomains", The FEBS journal 280, 2013, 2320-2331.

McFarland-Mancini, et al., "Differences in wound healing in mice with deficiency of IL-6 versus IL-6 receptor", Journal of immunology 184, 2010, 7219-7228.

Mohan, et al., "Recombinant human epidermal growth factor (REGEN-D 150): effect on healing of diabetic foot ulcers", Diabetes Research and Clinical Practice 78(3):405-411, 2007, 405-411.

Nam, et al., "Shedding of cell membrane-bound proteoglycans", Methods Mol Biol 836, 2012, 291-305.

Nanney, et al. , "Epidermal and dermal effects of epidermal growth factor during wound repair", The Journal of investigative dermatology 94, 1990, 624-629.

Parthasarathy, et al., "Robust flow measurement with multi-exposure speckle imaging", Optics express 16, 2008, 1975-1989.

Purushothaman, et al., "Heparanase-enhanced shedding of syndecan-1 by myeloma cells promotes endothelial invasion and angiogenesis", Blood 115, 2010, 2449-2457.

Richard, et al., "Effect of topical basic fibroblast growth factor on the healing of chronic diabetic neuropathic ulcer of the foot. A pilot, randomized, double-blind, placebo-controlled study", Diabetes care 18, 1995, 64-69.

Rodriguez-Manzaneque, et al., "Cleavage of syndecan-4 by ADAMTS1 provokes defects in adhesion.", The international journal of biochemistry & cell biology 41, 2009, 800-810.

Salmon-Ehr, et al., "Implication of Interleukin-4 in Wound Healing", Laboratory investigation; a journal of technical methods and pathology 80, 2000, 1337-343.

Sanberg, et al., "Monocyte transplantation for neural and cardiovascular ischemia repair", Journal of cellular and molecular medicine 14, 553-563, doi:10.1111/j.1582-4934.2009.00903.x (2010)., 2010, 553-563.

Seitz, et al., "Wound healing in mice with high-fat diet- or ob gene-induced diabetes—obesity syndromes: a comparative study", Experimental diabetes research 476969, 2010,.

Sica, et al., "Macrophage plasticity and polarization: in vivo veritas", The Journal of clinical investigation 122, 2012, 787-795.

Singh, et al., "Preventing foot ulcers in patients with diabetes. JAMA : the journal of the American Medical Association", JAMA 2, 217-228, 2005.

Slimani, et al., "Interaction of RANTES with syndecan-1 and syndecan-4 expressed by human primary macrophages", Biochimica et biophysica acta 1617, 2003, 80-88.

Smiell, et al., "Efficacy and safety of becaplermin (recombinant human platelet-derived growth factor—BB) in patients with nonhealing, lower extremity diabetic ulcers: a combined analysis of four randomized studies", Wound Repair Regen 7(5), 1999, 335-46.

Steed, et al., "Clinical evaluation of recombinant human platelet-derived growth factor for the treatment of lower extremity diabetic ulcers. Diabetic Ulcer Study Group", J Vasc Surg. Jan. 1995;21(1):71-8; discussion 79-81., 1995, 79-81.

Tsang, et al., "Human Epidermal Growth Factor Enhances Healing of Diabetic Foot Ulcers", Diabetes care 26, 2003, 1856-1861.

Van Weel, et al , "Hypercholesterolemia Reduces Collateral Artery Growth More Dominantly Than Hyperglycemia or Insulin Resistance in Mice", Arteriosclerosis, thrombosis, and vascular biology 26, 1383-1390, 2006, 1383-1390.

Wang, et al., "The mouse excisional wound splinting model, including applications for stem cell transplantation", Nature protocols 8, 2013, 302-309.

Wieman, et al., "Efficacy and safety of a topical gel formulation of recombinant human platelet-derived growth factor—BB (becaplermin) in patients with chronic neuropathic diabetic ulcers. A phase III randomized placebo-controlled double-blind study", Diabetes Care. 21(5), 1998, 822-7.

Xu, et al., "Stromal cell-derived factor-1 enhances wound healing through recruiting bone marrow-derived mesenchymal stem cells to the wound area and promoting neovascularization", Cells, tissues, organs 197, 2013, 103-113.

Zahorec, et al., "Mesenchymal stem cells for chronic wounds therapy", Cell and tissue banking 2014, 2014, 19-26.

\* cited by examiner

SYNDECAN-4 PROTEOLIPOSOMES FOR ENHANCED CUTANEOUS WOUND HEALING AND MINIMIZED INFLAMMATORY IMMUNE RESPONSE

CROSS-REFERENCE TO RELATED APPLICATIONS

This application claims benefit of U.S. Provisional Application No. 62/274,501, filed Jan. 4, 2016, which is hereby incorporated herein by reference in its entirety.

STATEMENT REGARDING FEDERALLY SPONSORED RESEARCH OR DEVELOPMENT

This invention was made with Government Support under Grant No. OD008716 awarded by the National Institutes of Health. The Government has certain rights in the invention.

BACKGROUND

Incidence of chronic non-healing wounds has significantly increased over the last decade due to a rising epidemic in type-2 diabetes and peripheral arterial disease (PAD). PAD has a prevalence of 202 million worldwide. Type-2 diabetes has been called the "epidemic of our generation" and the World Health Organization estimates that 347 million people suffer from diabetes worldwide. Neuropathy and microvascular angiopathy are common complications of diabetes and contribute to a 12-25% lifetime risk of developing diabetic ulcers. Diabetic ulcers are responsible for 25-50% of the total cost of diabetes treatment and are the most common cause for limb amputations in the United States. Diabetic ulcers are a complex clinical problem requiring a multifaceted treatment plan with standard therapeutic components including debridement of necrotic tissue, offloading, infection control, surgical revascularization, and limb elevation/compression. Current clinical standards provide relief from the symptoms but eventually fail in the long term, leaving patients with chronic ulcers and enhanced risk for limb amputation. Previous research has attempted to use growth factor proteins or genes to enhance the healing of cutaneous wounds but have achieved only limited success in clinical trials of healing chronic or recurring wounds in the long-term. Thus there is an immense need for an effective wound healing dressing for the growing patient population.

SUMMARY

Disclosed herein are compositions, articles, and methods for enhancing wound healing. In some embodiments, the disclosed methods involve co-delivering to the subject therapeutically effective amounts of a syndesome and a platelet derived growth factor (PDGF), wherein the co-delivery results in enhancement of wound healing. Therefore, also disclosed are compositions comprising syndesomes and PDGF polypeptides.

The term "syndesome" refers to a proteovesicle comprising a syndecan polypeptide embedded in a flexible carrier, such as a micelle or liposome. In some embodiments, the syndecan polypeptide comprises a wild-type or mutant syndecan-1 or a fragment thereof, a wild-type or mutant syndecan-2 or a fragment thereof, a wild-type or mutant syndecan-3 or a fragment thereof, a wild-type or mutant syndecan-4 or a fragment thereof. In some embodiments, the mutant syndecan comprises a mutation in a glycosaminoglycan-attachment site and/or a mutation in a residue recognized or cleaved by a sheddase, wherein the mutation decreases the ability of said mutant syndecan to be cleaved as compared to a corresponding wild-type syndecan.

In some embodiments, the syndesome further comprises PDGF receptors, such as PDGFRα, PDGFRβ, or combinations thereof. In some cases, the syndesome further comprises homodimers of PDGFRα, PDGFRβ, or combinations thereof. In some cases, the syndesomes further comprise heterodimers of PDGFRα and PDGFRβ.

Each proteovesicle can comprise from about 100 ng/ml up to about 100 μg/ml lipid, including about 100 ng/ml, 1 μg/ml, 10 μg/ml, 100 μg/ml, or any amount in-between. Each proteovesicle can comprise from about 5 ng/ml up to about 5 μg/ml syndecan, including about 5 ng/ml, 50 μg/ml, 500 ng/ml, 5 μg/ml, or any amount in-between. In some embodiments, the ratio of lipids to syndecan is preferably maintained as the amount of syndecan is adjusted.

In some embodiments, the PDGF polypeptide comprises a PDGF-AA, PDGF-BB, PDGF-CC, PDGF-DD protein, or a combination thereof. In some cases, the PDGF polypeptide comprises a heterodimer, such as PDGF-AA, PDGF-AB, PDGF-AC, PDGF-AD, PDGF-BB, PDGF-BC, PDGF-BD, PDGF-CC, or PDGF-CD. In some embodiments, the PDGF polypeptide comprises a human PDGF protein.

In some embodiments, the disclosed syndesomes are encapsulated along with the PDGF polypeptide into a biodegradable microcapsule or microbead for sustained co-release of the syndesomes and PDGF polypeptide in a subject. In some embodiments, the microcapsule or microbead comprises a biocompatible hydrogel, such as a polysaccharide hydrogel. For example, the microcapsule or microbead can comprise alginate gel, collagen gel, fibrin gel, poly(lactic-co-glycolic acid) (PLGA), or any mixture thereof. The microcapsules or microbeads can be any size suitable to encapsulate the syndesomes and PDGF polypeptide. For example, the microcapsules or microbeads can be from 1 μm in diameter, up to 3 mm in diameter, including about 1 μm to 100 μm, 100 μm to 1 mm, or 1 mm to 3 mm. The amount of syndesomes and PDGF polypeptide in the microcapsules or microbeads can be individually selected based upon release rates of the biodegradable microcapsules or microbeads, and requirements of the target tissue.

In some cases, the composition is a wound dressing. For example, the composition can be a liquid, semi-solid or solid composition for application directly to the surface of a wound. In some cases, the composition is applied to the surface of, or incorporated into, a solid wound contacting layer such as a wound dressing gauze or film. In some cases, the wound dressing composition is a fluid or a gel comprising the disclosed proteovesicle and PDGF polypeptide in combination with conventional pharmaceutical excipients for topical application to a wound. Suitable carriers include: Hydrogels containing cellulose derivatives, including hydroxyethyl cellulose, hydroxymethyl cellulose, carboxymethyl cellulose, hydroxypropylmethyl cellulose and mixtures thereof; and hydrogels containing polyacrylic acid (Carbopols). Suitable carriers also include creams/ointments used for topical pharmaceutical preparations, e.g. creams based on cetomacrogol emulsifying ointment. The above carriers may include alginate (as a thickener or stimulant), preservatives such as benzyl alcohol, buffers to control pH such as disodium hydrogen phosphate/sodium dihydrogen phosphate, agents to adjust osmolarity such as sodium chloride, and stabilisers such as EDTA.

As used herein, the disclosed wound can result from, for example, a scrape, cut, laceration wound, crush wound, compression wound, stretch injury, bite wound, graze, bullet wound, explosion injury, body piercing, stab wound, burn wound, wind burn, sun burn, chemical burn, surgical wound, surgical intervention, medical intervention, host rejection following cell, tissue or organ grafting, pharmaceutical effect, pharmaceutical side-effect, bed sore, radiation injury, cosmetic skin wound, internal organ injury, disease process (e.g., asthma, cancer), infection, infectious agent, developmental process, maturational process (e.g., acne), genetic abnormality, developmental abnormality, environmental toxin, allergen, scalp injury, facial injury, jaw injury, foot injury, toe injury, finger injury, bone injury, sex organ injury, joint injury, excretory organ injury, eye injury, corneal injury, muscle injury, adipose tissue injury, lung injury, airway injury, hernia, anus injury, piles, ear injury, retinal injury, skin injury, abdominal injury, arm injury, leg injury, athletic injury, back injury, birth injury, premature birth injury, toxic bite, sting, tendon injury, ligament injury, heart injury, heart valve injury, vascular system injury, cartilage injury, lymphatic system injury, craniocerebral trauma, dislocation, esophageal perforation, fistula, nail injury, foreign body, fracture, frostbite, hand injury, heat stress disorder, laceration, neck injury, self-mutilation, shock, traumatic soft tissue injury, spinal cord injury, spinal injury, sprain, strain, tendon injury, ligament injury, cartilage injury, thoracic injury, tooth injury, trauma, nervous system injury, aging, aneurism, stroke, digestive tract injury, infarct, or ischemic injury. In some cases, the wound is a skin wound. In particular embodiments, the wound is a chronic wound, such as a venous ulcer, pressure sore, decubitis ulcer, diabetic ulcers, or chronic ulcer of unknown etiology.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
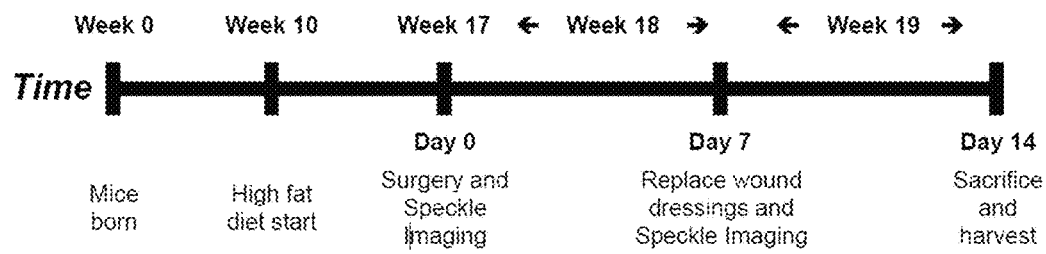
FIG. 1 is an experimental timeline for evaluating wound healing in mice.

The disclosed compositions and methods involve the co-delivery of a syndesome and a PDGF polypeptide to promote wound healing. The term "syndesome" refers to a proteovesicle comprising a recombinant syndecan polypeptide embedded in a flexible carrier.

Syndecans are a class of cell surface heparan sulfate proteoglycans (HSPGs) that mediate the interaction of growth factors and their receptors. Also disclosed are peptide variants and/or fragments of naturally occurring syndecans. For example, the disclosed syndesomes can include peptides having amino acid sequences that are at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to a naturally occurring sequence, such as the reference sequences disclosed herein.

The syndecans can be extracted from natural sources or produced synthetically or recombinantly.

In some embodiments, a mutant syndecan is used that comprises a mutation in a residue recognized and/or cleaved by a sheddase, wherein the mutation decreases the ability of said mutant syndecan to be cleaved by a sheddase as compared to a corresponding wild-type syndecan. A sheddase may be any protease capable of cleaving the extracellular, or ectodomain, of a syndecan. For example, the juxtamembrane domain may be mutated to be resistant to proteolytic cleavage. For instance, one region of syndecan-1 known to be susceptible to proteolytic cleavage is the region between Gln238 and Gln252. This region could be replaced by a similar region from another syndecan that does not become cleaved, or individual cleavage sites could be mutated.

In some embodiments, a mutant syndecan comprises a mutation in the cytoplasmic tail. For example, any serine or tyrosine can be mutated to alanine or phenylalanine to mimic a constitutive state of dephosphorylation or to aspartic acid or glutamic acid to mimic a constitutive state of phosphorylation. Other mutations can be made to affect intracelluar signaling via interactions with other proteins. For example, the C1 domain of the cytoplasmic tail of a syndecan can be mutated to affect interactions with proteins such as cortactin, src, tubulin or ezrin. The V domain can be mutated to affect interactions with proteins such as syndesmos, PKC-α, α-actinin, for example. The C2 domain can be mutated to affect interactions with proteins such as synectin, syntenin, CASK or synbindin, for example. Mutations can be made to disrupt association between a syndecan and the aforementioned proteins or other proteins known to interact with syndecans. Mutations can be made that increase association between a syndecan and the aforementioned proteins or other proteins known to interact with syndecans. Additionally, mutations can be made that alter the physical conformation of the syndecan and/or the associated protein(s) to affect the resulting process of intracellular signaling.

A flexible carrier may be any material suitable for delivering a transmembrane polypeptide to the membrane of a cell. Modifications may be made to a flexible carrier to increase the efficiency with which the flexible carrier delivers a polypeptide to a cell, for example, by changing the ratio of materials present in the flexible carrier. A flexible carrier may be a lipid-based vehicle. For example, a flexible carrier may comprise lipids suitable for delivering one or more polypeptides to a cell, preferably by means of the fusion of the flexible carrier with the cell.

A lipid vesicle may comprise phospholipids, glycolipids, steroids, or synthetic lipid analogues (e.g., amphipathic, synthethic polymers, such as poly(2-methyl-2-oxazoline) (PMOZ) and poly(2-ethyl-2-oxazoline) (PEOZ)). A lipid vesicle that comprises phospholipids may exist as a monolayer or a bilayer. Modifications may be made to a lipid-based vehicle to increase the efficiency with which the lipid vesicle fuses with a cell, for example, by changing the lipid content. A lipid vesicle may be a micelle or a bacterial or red cell ghost. A lipid vesicle may be vesicles or membrane fragments of transgenic cells. The lipid vesicle may be a liposome, which is a general category of vesicle that may comprise one or more lipid bilayers surrounding an aqueous space. Liposomes include unilamellar vesicles composed of a single membrane or a lipid bilayer, and multilamellar vesicles (MLVs) composed of many concentric membranes (or lipid bilayers). Methods for liposome production are well known in the art (see U.S. Pat. No. 6,248,353, for example).

A flexible carrier may also have few or no lipid components. Examples of non-lipid transmembrane polypeptide carriers are described in U.S. Pat. No. 6,492,501, the contents of which are hereby incorporated by reference. A flexible carrier may comprise amphiphilic peptide polymers such as peptitergents, or modified amphiphilic polyacrylates, for example.

According to some embodiments, the flexible carrier may have one or more polypeptides embedded within. All that is required for a polypeptide to be considered embedded within a flexible carrier is that a portion of the polypeptide, for example, hydrophobic residues of the polypeptide, be in contact with the hydrophobic moieties such that the polypeptide is stably associated with the flexible carrier. In some embodiments, the flexible carrier may be a liposome in which a syndecan polypeptide is embedded by means of the hydrophobic interactions between the transmembrane region of the syndecan and the lipid bilayer of the liposome.

A transmembrane region is any region of a protein capable of becoming inserted or embedded into an area of hydrophobicity, for example, a lipid membrane. An area of hydrophobicity may be the lipid bilayer of a cell membrane or a liposome, for example. A transmembrane region may also be referred to as a transmembrane domain or integral membrane domain, for example. A protein comprising a transmembrane region may be referred to as a membrane protein, a transmembrane protein or an integral membrane protein, for example. Transmembrane proteins typically comprise a transmembrane domain and either an extracellular domain, an intracellular domain, or both. An extracellular domain may be referred to by other terms well known in the art, including, for example, an ectodomain. An intracellular domain of a protein expressed in a cell is in contact with the cell's cytoplasm and is therefore also called a cytoplasmic domain or a cytoplasmic tail. Transmembrane regions may comprise hydrophobic residues and/or show alpha-helical secondary structure. Methods for predicting whether a region of a protein may act as a transmembrane region are well known in the art (for example, see Cao et al., Bioinformatics, 22(3): 303-309, (2006)).

The disclosed compositions and methods provide for the co-delivery of a syndesome and a PDGF polypeptide to a cell. All that is required by the term "co-delivery" is that both the syndesome and the PDGF polypeptide be delivered to a cell. Co-delivery may occur simultaneously or at discrete time points. The syndesome and PDGF polypeptide may physically interact previous to the providing step or may interact subsequent to the providing step. In some embodiments, the syndesome and PDGF polypeptide are present in the same composition or formulation.

The disclosed syndesomes and PDGF polypeptides can be encapsulated together in a microcapsule or microbead. For example, in some embodiments, the microcapsule or microbead comprises a biocompatible hydrogel.

Compositions that form hydrogels generally fall into three classes. The first class carries a net negative charge and is typified by alginate. The second class carries a net positive charge and is typified by extracellular matrix components, such as collagen and laminin. Examples of commercially available extracellular matrix components include Matrigel™ and Vitrogen™. The third class is net neutral in charge. An example of a net neutral hydrogel is highly crosslinked polyethylene oxide, or polyvinylalcohol.

Examples of materials which can be used to form a suitable hydrogel include polysaccharides such as alginate, polyphosphazines, poly(acrylic acids), poly(methacrylic acids), poly(alkylene oxides), poly(vinyl acetate), poly (acrylamides) such as poly(N-isopropylacrylamide), polyvinylpyrrolidone (PVP), and copolymers and blends of each. In some embodiments, block copolymers can be used. For example, poloxamers containing a hydrophobic poly(alkylene oxide) segment (i.e., polypropylene oxide) and hydrophilic poly(alkylene oxide) segment (i.e., polyethylene oxide) can be used. Polymers of this type are available are known in the art, and commercially available under the trade name PLURONICS from BASF. In some embodiments, the material is selected such that it forms a thermally responsive hydrogel.

In general, the polymers are at least partially soluble in aqueous solutions, such as water, buffered salt solutions, or aqueous alcohol solutions. In some embodiments, the polymers have polar groups, charged groups, acidic groups or salts thereof, basic groups or salts thereof, or combinations thereof. Examples of polymers with acidic groups poly (phosphazenes), poly(acrylic acids), poly(methacrylic acids), poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups include carboxylic acid groups and sulfonic acid groups.

Examples of polymers with basic groups include poly (vinyl amines), poly(vinyl pyridine), poly(vinyl imidazole), and some imino substituted polyphosphazenes. Nitrogen-containing groups in these polymers can be converted to ammonium or quaternary salts. Ammonium or quaternary salts can also be formed from the backbone nitrogens or pendant imino groups. Examples of basic groups include amino and imino groups.

In certain embodiments, the biocompatible hydrogel-forming polymer is a water-soluble gelling agent. In certain embodiments, the water-soluble gelling agent is a polysaccharide gum, such as a polyanionic polysaccharide. In some cases, syndesomes and one or more growth factors are encapsulated using an anionic polymer such as alginate to form a microcapsule.

Mammalian and non-mammalian polysaccharides have been explored for cell encapsulation. These materials can be used, alone or in part, to form the microcapsule. Exemplary polysaccharides include alginate, chitosan, hyaluronan (HA), and chondroitin sulfate. Alginate and chitosan form crosslinked hydrogels under certain solution conditions, while HA and chondroitin sulfate are preferably modified to contain crosslinkable groups to form a hydrogel.

In some embodiments, the microcapsule or microbead comprises alginate or derivative thereof. Alginates are a family of unbranched anionic polysaccharides derived primarily from brown algae which occur extracellularly and intracellularly at approximately 20% to 40% of the dry weight. The 1,4-linked $\alpha$-1-guluronate (G) and $\beta$-D-mannuronate (M) are arranged in homopolymeric (GGG blocks and MMM blocks) or heteropolymeric block structures (MGM blocks). Cell walls of brown algae also contain 5% to 20% of fucoidan, a branched polysaccharide sulphate ester with 1-fucose four-sulfate blocks as the major component. Commercial alginates are often extracted from algae washed ashore, and their properties depend on the harvesting and extraction processes. Although the properties of the hydrogel can be controlled to some degree through changes in the alginate precursor (molecular weight, composition, and macromer concentration), alginate does not degrade, but rather dissolves when the divalent cations are replaced by monovalent ions. In addition, alginate does not promote cell interactions.

Alginate can form a gel in the presence of divalent cations via ionic crosslinking. Crosslinking can be performed by addition of a divalent metal cation (e.g., a calcium ion or a barium ion), or by cross-linking with a polycationic polymer (e.g., an amino acid polymer such as polylysine). See e.g., U.S. Pat. Nos. 4,806,355, 4,689,293 and 4,673,566 to Goosen et al.; U.S. Pat. Nos. 4,409,331, 4,407,957, 4,391,909 and 4,352,883 to Lim et al.; U.S. Pat. Nos. 4,749,620 and 4,744,933 to Rha et al.; and U.S. Pat. No. 5,427,935 to Wang et al. Amino acid polymers that may be used to crosslink hydrogel forming polymers such as alginate include the cationic poly(amino acids) such as polylysine, polyarginine, polyornithine, and copolymers and blends thereof.

In some embodiments, the microcapsule or microbead comprises chitosan or derivative thereof. Chitosan is made by partially deacetylating chitin, a natural non-mammalian polysaccharide, which exhibits a close resemblance to mammalian polysaccharides, making it attractive for cell encapsulation. Chitosan degrades predominantly by lysozyme through hydrolysis of the acetylated residues. Higher degrees of deacetylation lead to slower degradation times, but better cell adhesion due to increased hydrophobicity. Under dilute acid conditions (pH<6), chitosan is positively charged and water soluble, while at physiological pH, chitosan is neutral and hydrophobic, leading to the formation of a solid physically crosslinked hydrogel. The addition of polyol salts enables encapsulation of cells at neutral pH, where gelation becomes temperature dependent. Chitosan has many amine and hydroxyl groups that can be modified. For example, chitosan has been modified by grafting methacrylic acid to create a crosslinkable macromer while also grafting lactic acid to enhance its water solubility at physiological pH. This crosslinked chitosan hydrogel degrades in the presence of lysozyme and chondrocytes. Photopolymerizable chitosan macromer can be synthesized by modifying chitosan with photoreactive azidobenzoic acid groups. Upon exposure to UV in the absence of any initiator, reactive nitrene groups are formed that react with each other or other amine groups on the chitosan to form an azo crosslink.

In some embodiments, the microcapsule or microbead comprises hyaluronan or derivative thereof. Hyaluronan (HA) is a glycosaminoglycan present in many tissues throughout the body that plays an important role in embryonic development, wound healing, and angiogenesis. In addition, HA interacts with cells through cell-surface receptors to influence intracellular signaling pathways. Together, these qualities make HA attractive for tissue engineering scaffolds. HA can be modified with crosslinkable moieties, such as methacrylates and thiols, for cell encapsulation. Crosslinked HA gels remain susceptible to degradation by hyaluronidase, which breaks HA into oligosaccharide fragments of varying molecular weights. Auricular chondrocytes can be encapsulated in photopolymerized HA hydrogels where the gel structure is controlled by the macromer concentration and macromer molecular weight. In addition, photopolymerized HA and dextran hydrogels maintain long-term culture of undifferentiated human embryonic stem cells. HA hydrogels have also been fabricated through Michael-type addition reaction mechanisms where either acrylated HA is reacted with PEG-tetrathiol, or thiol-modified HA is reacted with PEG diacrylate.

Chondroitin sulfate makes up a large percentage of structural proteoglycans found in many tissues, including skin, cartilage, tendons, and heart valves, making it an attractive biopolymer for a range of tissue engineering applications. Photocrosslinked chondroitin sulfate hydrogels can be been prepared by modifying chondroitin sulfate with methacrylate groups. The hydrogel properties were readily controlled by the degree of methacrylate substitution and macromer concentration in solution prior to polymerization. Further, the negatively charged polymer creates increased swelling pressures allowing the gel to imbibe more water without sacrificing its mechanical properties. Copolymer hydro gels of chondroitin sulfate and an inert polymer, such as PEG or PVA, may also be used.

In some embodiments, the microcapsule or microbead comprises a hydrogel that mimics an extracellular matrix (ECM). Components of an extracellular matrix can include for example collagen, fibrin, fibrinogen, thrombin, elastin, laminin, fibronectin, hyaluronic acid, chondroitin 4-sulfate, chondroitin 6-sulfate, dermatan sulfate, heparin sulfate, heparin, and keratan sulfate, and proteoglycans.

In some embodiments, the microcapsule or microbead comprises a synthetic polymer or polymers. Polyethylene glycol (PEG) has been the most widely used synthetic polymer to create macromers for cell encapsulation. A number of studies have used poly(ethylene glycol)di(meth) acrylate to encapsulate a variety of cells. Biodegradable PEG hydrogels can be been prepared from triblock copolymers of poly($\alpha$-hydroxy esters)-b-poly(ethylene glycol)-b- poly(α-hydroxy esters) endcapped with (meth)acrylate functional groups to enable crosslinking. PLA and poly(8-caprolactone) (PCL) have been the most commonly used poly(α-hydroxy esters) in creating biodegradable PEG macromers for cell encapsulation. The degradation profile and rate are controlled through the length of the degradable block and the chemistry. The ester bonds may also degrade by esterases present in serum, which accelerates degradation. Biodegradable PEG hydrogels can also be fabricated from precursors of PEG-bis-[2-acryloyloxy propanoate]. As an alternative to linear PEG macromers, PEG-based dendrimers of poly(glycerol-succinic acid)-PEG, which contain multiple reactive vinyl groups per PEG molecule, can be used. An attractive feature of these materials is the ability to control the degree of branching, which consequently affects the overall structural properties of the hydrogel and its degradation. Degradation will occur through the ester linkages present in the dendrimer backbone.

In some cases, the hydrogel-forming material is selected from the group consisting of poly-lactic-co-glycolic acid (PLGA), poly-1-lactide (PLLA), poly-caprolactone (PCL), polyglycolide (PGA), derivatives thereof, copolymers thereof, and mixtures thereof.

The biocompatible, hydrogel-forming polymer can contain polyphosphoesters or polyphosphates where the phosphoester linkage is susceptible to hydrolytic degradation resulting in the release of phosphate. For example, a phosphoester can be incorporated into the backbone of a crosslinkable PEG macromer, poly(ethylene glycol)-di-[ethyl-phosphatidyl (ethylene glycol) methacrylate] (PhosPEG-dMA), to form a biodegradable hydrogel. The addition of alkaline phosphatase, an ECM component synthesized by bone cells, enhances degradation. The degradation product, phosphoric acid, reacts with calcium ions in the medium to produce insoluble calcium phosphate inducing autocalcification within the hydrogel. Poly(6-aminoethyl propylene phosphate), a polyphosphoester, can be modified with methacrylates to create multivinyl macromers where the degradation rate was controlled by the degree of derivitization of the polyphosphoester polymer.

Polyphosphazenes are polymers with backbones consisting of nitrogen and phosphorous separated by alternating single and double bonds. Each phosphorous atom is covalently bonded to two side chains. The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Hydrolytically stable polyphosphazenes are formed of monomers having carboxylic acid side groups that are crosslinked by divalent or trivalent cations such as $Ca^{2+}$ or $Al^{3+}$. Polymers can be synthesized that degrade by hydrolysis by incorporating monomers having imidazole, amino acid ester, or glycerol side groups. Bioerodible polyphosphazines have at least two differing types of side chains, acidic side groups capable of forming salt bridges with multivalent cations, and side groups that hydrolyze under in vivo conditions, e.g., imidazole groups, amino acid esters, glycerol and glucosyl. Hydrolysis of the side chain results in erosion of the polymer. Examples of hydrolyzing side chains are unsubstituted and substituted imidizoles and amino acid esters in which the group is bonded to the phosphorous atom through an amino linkage (polyphosphazene polymers in which both R groups are attached in this manner are known as polyaminophosphazenes). For polyimidazolephosphazenes, some of the "R" groups on the polyphosphazene backbone are imidazole rings, attached to phosphorous in the backbone through a ring nitrogen atom.

Disclosed are methods for enhancing wound healing in a subject by administering to the subject a syndesome and PDGF polypeptide as disclosed herein. There are three main types of chronic wounds: venous ulcers, diabetic ulcers, and pressure ulcers. Venous ulcers usually occur in the legs, account for the majority of chronic wounds, and mostly affect the elderly. They are caused by improper function of tiny valves in the veins that normally prevent blood from flowing backward. The dysfunction of these valves impedes the normal circulation of blood in the legs, causing tissue damage and impaired wound healing. Diabetic patients are particularly susceptible to developing ulcers. People with advanced diabetes have a diminished perception of pain in the extremities due to nerve damage, and therefore may not initially notice small scratches or bruises on their legs and feet. Diabetes also impairs the immune system and damages capillaries. Repeated injury, compounded by impaired healing, can cause even the smallest cut or bruise to become dangerously infected. Pressure ulcers comprise the third main type of chronic wounds. These typically occur in people who are bedridden or whose mobility is severely limited. Pressure ulcers are caused by a loss of blood circulation that occurs when pressure on the tissue is greater than the pressure in capillaries, thereby cutting off circulation. Parts of the body that are particularly susceptible to pressure ulcers include the heels, shoulder blades, and sacrum (the triangular bone at the base of the spine forming the posterior of the pelvis).

The disclosed syndesome and PDGF compositions, including microcapsules encapsulating syndesomes and PDGF, can be used therapeutically in combination with a pharmaceutically acceptable carrier. Pharmaceutical carriers are known to those skilled in the art. These most typically would be standard carriers for administration of drugs to humans, including solutions such as sterile water, saline, and buffered solutions at physiological pH. The compositions can be administered intraperitonealy, topically, intramuscularly, or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, anti-inflammatory agents, anesthetics, and the like.

The pharmaceutical composition can be administered in a number of ways depending on whether local or systemic treatment is desired, and on the area to be treated. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter-indications. Dosage can vary, and can be administered in one or more dose administrations daily, for one or several days.

The herein disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

The term "alginate" refers to linear polysaccharides formed from β-D-mannuronate and β-L-guluronate in any M/G ratio, as well as salts and derivatives thereof.

The term "amino acid sequence" refers to a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

The term "biocompatible" refers to a material and any metabolites or degradation products thereof that are generally non-toxic to the recipient and do not cause any significant adverse effects to the subject.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "hydrogel" refers to a substance formed when an organic polymer (natural or synthetic) is cross-linked via covalent, ionic, or hydrogen bonds to create a three-dimensional open-lattice structure which entraps water molecules to form a gel. Biocompatible hydrogel refers to a polymer that forms a gel which is not toxic to living cells, and allows sufficient diffusion of oxygen and nutrients to the entrapped cells to maintain viability.

The term "lipid vesicle" refers to a small vesicle composed of various types of lipids, phospholipids and/or surfactant that can be embedded with a syndesome disclosed herein.

The term "liposome" refers to vesicle composed of a lipid bilayer.

The term "micelle" refers to vesicle composed of a lipid monolayer.

The term "microcapsule" refers to a particle or capsule having a mean diameter of about 50 μm to about 1000 μm, formed of a cross-linked hydrogel shell surrounding a biocompatible matrix. The microcapsule may have any shape suitable for cell encapsulation. The microcapsule may contain one or more cells dispersed in the biocompatible matrix, cross-linked hydrogel, or combination thereof, thereby "encapsulating" the cells.

The terms "peptide," "protein," and "polypeptide" are used interchangeably to refer to a natural or synthetic molecule comprising two or more amino acids linked by the carboxyl group of one amino acid to the alpha amino group of another. In addition, the terms refer to amino acids joined to each other by peptide bonds or modified peptide bonds, e.g., peptide isosteres, etc. and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation.

The term "percent (%) sequence identity" or "homology" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "promote" refers to an increase in an activity, response, condition, disease, or other biological parameter. This can include but is not limited to the initiation of the activity, response, condition, or disease. This may also include, for example, a 10% increase in the activity, response, condition, or disease as compared to the native or control level. Thus, the reduction can be a 10, 20, 30, 40, 50, 60, 70, 80, 90, 100%, or any amount of increase in between as compared to native or control levels.

The term "proteovesicle" refers to lipid vesicle or particle comprising a protein embedded in the membrane or attached to its surface.

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The terms "transformation" and "transfection" mean the introduction of a nucleic acid, e.g., an expression vector, into a recipient cell including introduction of a nucleic acid to the chromosomal DNA of said cell.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, 95%, 96%, 97%, 98%, or 99% sequence identity to a reference sequence.

The term "vector" or "construct" refers to a nucleic acid sequence capable of transporting into a cell another nucleic acid to which the vector sequence has been linked. The term "expression vector" includes any vector containing a gene construct in a form suitable for expression by a cell (e.g., operably linked to a transcriptional control element).

A number of embodiments of the invention have been described. Nevertheless, it will be understood that various modifications may be made without departing from the spirit and scope of the invention. Accordingly, other embodiments are within the scope of the following claims.

EXAMPLES

Example 1

Methods

Syndecan-4 overexpression and purification. The full-length syndecan-4 gene was incorporated into HEK 293Ta cells using lentiviral transduction and a custom made plasmids (Genecopoeia). The stably overexpressing cells were grown in large amounts and lysed using cold lysis buffer containing 1% Triton X-100 (SIGMA) and protease inhibitors (Roche). The cold cell lysate was triturated with 16, 18, 20 and 22G needles to reduce the viscosity of the lysate and then sonicated 3 times for 1 minute while being kept on ice in between sonications. The lysate was ultra-centrifuged at 25,000×g to result in a clear non-viscous supernatant. The supernatant was collected in a fresh tube and the protein was purified using a HiTrap Q HP column (GE Healthcare) on a FPLC (Amersham Biosciences). The pure protein was confirmed by silver stain (Pierce SilverStain Kit—Thermo Scientific) and a western blot for syndecan-4 antibody (Abcam). Finally the protein was quantified using the Pierce BCA assay (Thermo Scientific).

Preparation of proteoliposomes. Stock solutions of the following lipids were made at 10 mg/ml in chloroform: 1,2-dioleoyl-sn-glycero-3-phosphocholine (DOPC), 1,2-dioleoyl-sn-glycero-3-phosphoethanolamine (DOPE), cholesterol, and sphingomyelin (Avanti Polar Lipids). The lipids were mixed in the volumetric ratio of 2:1:1:1 (DOPC:DOPE:Chol:Sphingo), in a round bottom glass flask. The chloroform was evaporated from the mixture using a rotatory evaporator for 1 hour, followed by a stream of argon gas for 15 minutes to remove the last traces of chloroform. The lipid film was resuspended in a HEPES-buffered salt solution by vortexing, sonicating and freeze-thawing three times each, in order. The resulting lipid solution was extruded through the 400 nm polycarbonate membrane filter (Avestin) to make the final liposomes. In order to incorporate the syndecan-4 protein into the membrane and make syndesomes, the syndecan-4 protein solution (50 ug/ml) was added to the liposomes containing 1% n-octyl-B-D-glucopyranoside (Sigma). The detergent was removed through serial dilution and overnight dialysis with PBS containing Bio-Beads (SM-2, Bio-Rad). PDGF-BB (Peprotech) was mixed with the syndesomes exogenously when they were delivered together. For imaging with cryo-electron microscopy, the liposomes were plunge-frozen in liquid ethane on carbon holey film grids as previously described (R2×2 Quantifoil®; Micro Tools GmbH, Jena, Germany). The grids were transferred to a cryo-specimen holder (Gatan 626) under liquid nitrogen and put in a microscope (JEOL 2100 LaB6) operating at 200 keV. Grids were maintained at close to liquid nitrogen temperatures during EM session (−172° C. to −180° C.). Liposomes were imaged at 20,000×EM magnification with a 4k×4k slow-scan CCD camera (UltraScan 895, GATAN, Inc.) using low-dose imaging procedure. Images were acquired with less than 20 electrons/Å$^2$ electron dose.

Production of sustained release alginate disks. A custom machined mold was used to create 6.35 mm diameter alginate disks with the treatments encapsulated in them. Briefly, equal volumes of 4% sodium alginate (Sigma) solution and 0.85% NaCl solution were mixed and the treatments added accordingly. This solution was pipetted into the mold and crosslinked with 1.1% CaCl$_2$ (Sigma) for 1 hour at 4° C. 5 μg of PDGF-BB and/or 0.5 μg of syndecan-4 protein was used according to the sample (control, PDGF-BB, S4PL (syndesomes) or S4PL with PDGF-BB) in each disk implanted. The alginate disks were flash frozen in liquid nitrogen (−195 C) and lyophilized overnight (−110 C, 0.0005 mbar) in scintillation vials. The final freeze-dried gels were sputter coated with gold discharge for 30 seconds and then imaged using the scanning electron microscope (FEI Quanta 650 ESEM) at 10 kV.

Electric cell-substrate impedance sensing (ECIS) assay for keratinocyte migration. The 96W1E+ plates (96 wells) were first coated with 100 μl of 2 mM Cysteine (Sigma) per well for 30 minutes followed by a quick wash with 1×PBS. The wells were then coated with 40 μl/well of fibronectin (Sigma) at 8 μg/ml overnight. After a quick 1× PBS wash, to remove unbound fibronectin, the cells were plated at 10,000 cells per well and allowed to attach, while the plate was placed on the Z-Theta instrument (ECIS), which created an electric fence around the electrode. The cells used for the assay were adult dermal fibroblasts and adult epidermal keratinocytes, both from either healthy or type 2 diabetic donors (Lonza). The version of software used to run the machine was Version 1.2.173.0 PC. The cells were allowed to settle and attach for 4 hours. Finally, the electric fence was turned off and the cells were allowed to migrate over the electrode. The substrate impedance and resistance were measured every 48 seconds at a frequency of 40,000 Hz. The data was collected over 24 hours and analyzed using Microsoft Excel.

Fibroblast invasion assays. Human adult dermal fibroblasts (Lonza) were used in the Trevigen Inc. Collagen-I cell invasion assay to assess the invasion potential of the fibroblasts in the presence of various treatments. The cells were starved in a serum free media for 24 hours before the experiment. The top invasion chamber was coated with collagen-I and kept to attach overnight. The cells were plated in each well at 10$^6$ cells/ml concentration in the top chamber while treatments were added to the bottom chamber. The cells were incubated with the treatments for 24 hours and then the top chambers were moved to the assay plate with Calcein-AM and cell dissociation solution. This solution detaches the cells that have invaded from the top chamber to the bottom side. Finally the assay plate was read without the top chamber at 485 nm excitation and 520 nm emission. The intensity is a measure of the amount of cell invasion through the collagen-I layer.

Animal studies. All animal experiments were performed with the approval of the Institutional Animal Care and Use Committee (IACUC) of University of Texas at Austin, and in accordance with NIH guidelines "Guide for Care and Use of Laboratory Animals" for animal care. All the animal experiments were performed on a diabetic, obese and hyperlipidemic mouse model (ob/ob). All the ob/ob mice (B6.Cg-Lepob/J) were purchased from the Jackson Laboratory. All animals were fed a high fat diet (Research Diets—D12331) for 10 weeks before performing wound healing surgeries.

Excisional wound healing model. To examine wound healing in the diabetic and obese mice a full-thickness excisional model was used with a splint to prevent wound contraction. A sterile 5-mm biopsy punch was used to outline a pattern of four wounds, two on either side of midline on the dorsum of the mouse. A splint was fashioned using 0.5-mm thick silicone sheet and was placed so that the wound was centered within the splint. The splint was immobilized in place using 6-0 nylon sutures and cyanoacrylate glue to prevent wound contraction. Alginate gel disks encapsulating syndesomes and/or PDGF-BB were then applied directly to the region of the open wound. A single sheet of Tegaderm was used to cover all the wounds. Photographs of the wounds were taken on days 0, 7 and 14. The animals were euthanized at 14 days, and the wounds were biopsied with a 10-mm biopsy punch. The tissues were snap frozen in liquid N2-chilled isopentane and used for further analysis.

Histological analysis and immunostaining. Tissues from the in vivo experiments were embedded in paraffin and 6 μm thick sections were produced using a microtome. The slides were stained with H&E or Movat's pentachrome stains. The wound healing samples were also immunostained using the Envision+ Dual Link Kit (Dako North America, Inc.) for cytokeratin (Abcam), M1 macrophage marker—CD86 (Bioss), M2 macrophage marker—CD163 (Bioss) or von Willebrand factor (Dako). Briefly, the slides were de-paraffinized and placed in a bucket with Antigen Retrieval Solution (Dako), and placed in the microwave (1250 W) for 2 minutes and 40 seconds. Then the bucket was placed in a water bath maintained at 80° C. for 3 hours. This reduces the background staining significantly. The slides were cooled in solution for 20 minutes and washed in PBS twice for 5 minutes each. Then they were blocked in 20% fetal bovine serum in PBS for 45 minutes at room temperature. The slides were then washed two times for 5 minutes in PBS and a circle was drawn around the section with a hydrophobic pen. The sections were peroxide blocked with dual enzyme block solution (Dako) and incubated for 30 minutes. This was followed by 3 washes in PBS for 5 minutes each. After that, the primary antibody in antibody diluent (Dako) was applied to the sections and the slides were incubated at 4° C. for overnight. On the following day, the sections were washed in PBS thrice and then the peroxidase labeled polymer (HRP) was added and the slides were incubated for 30 minutes at room temperature. Following the incubation, nine washes with PBS were done after with a wait of 5 minutes after every 3 washes. In the meantime, the DAB+ solution was prepared and added to the sections once washing had been completed. The incubation period was optimized according to the intensity of staining. After 3 washes in PBS, the slides were stained in Mayer's Hematoxylin for 3 minutes. Finally they were washed in distilled water three times, mounted with an aqueous mounting media and covered with a cover glass.

Statistical Analysis. All results are shown as mean±standard error of the mean. Comparisons between only two groups were performed using a 2-tailed Student's t-test. Differences were considered significant at $p<0.05$. Multiple comparisons between groups were analyzed by 2-way ANOVA followed by a Tukey post-hoc test. A 2-tailed probability value <0.05 was considered statistically significant.

Results

Figure 2:
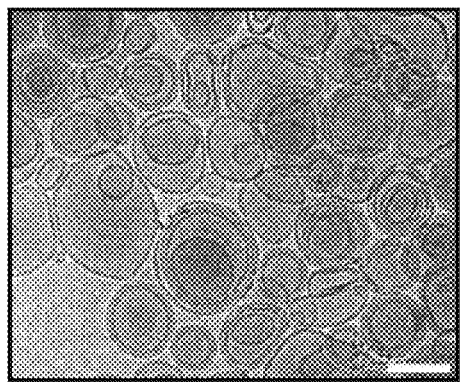
FIG. 2 is an imaging showing Cryo EM of liposomes and syndesomes.
Figure 2:
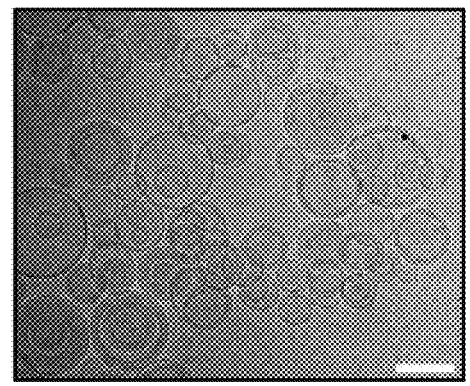
Figure 2:
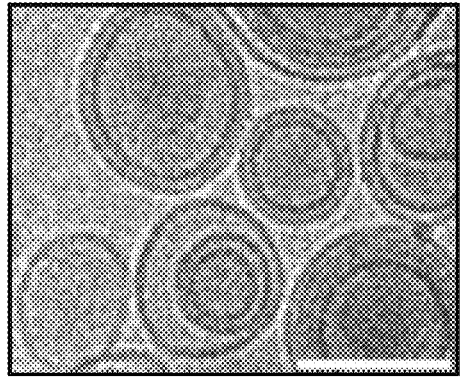
Figure 2:
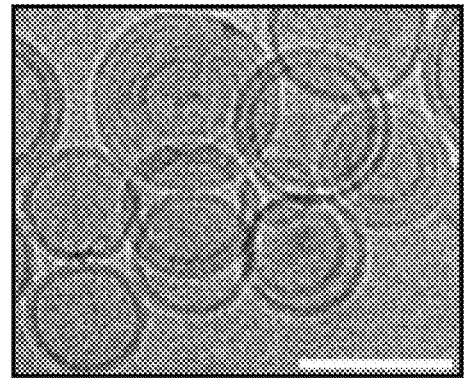
Figure 3:
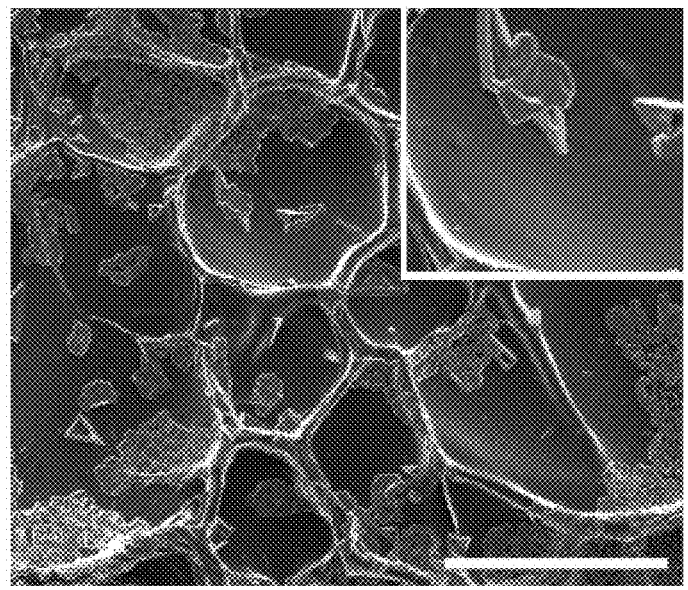
FIG. 3 is an image showing SEM of lyophilized alginate with and without syndesomes (S4PL).
Figure 3:
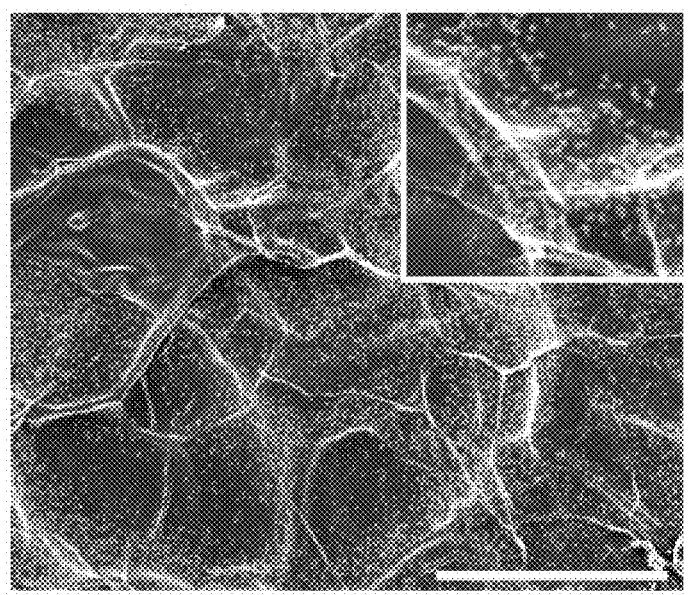
Figure 4:
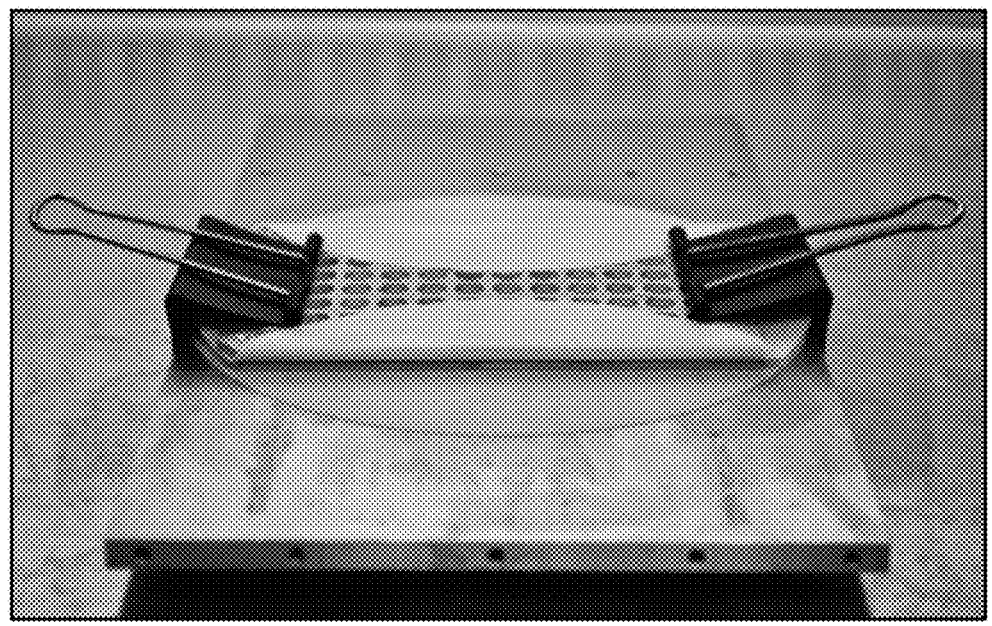
FIG. 4 is an image of the custom made mold to prepare the alginate wound dressings for the mice surgery. Bottom figure shows the alginate disk encapsulating the treatment, which is then placed in the wound.
Figure 4:
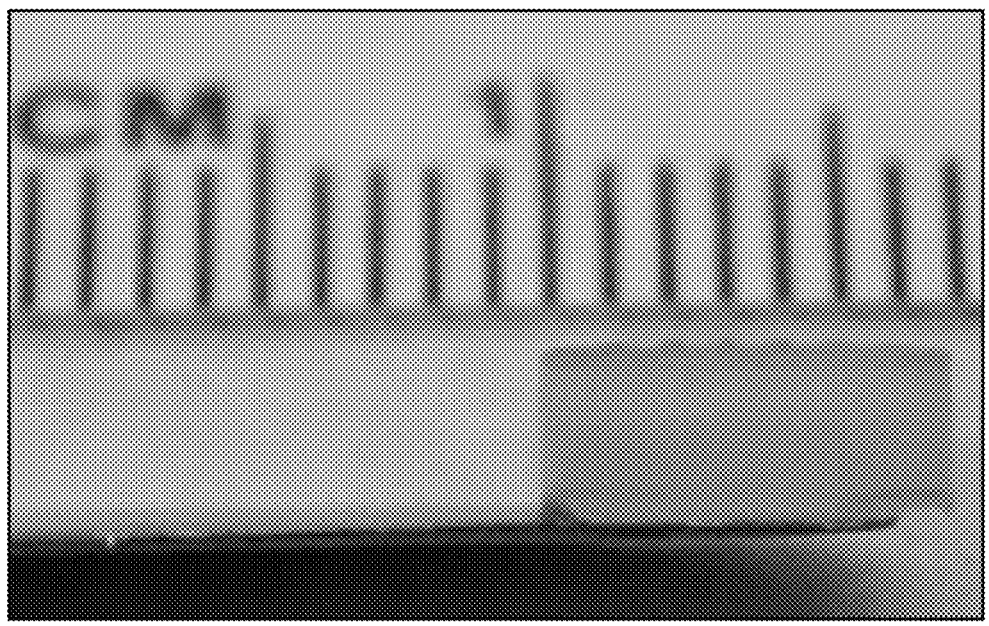

Syndesomes were created by isolating recombinant syndecan-4 proteins and fusing them into the membrane of liposomes using a detergent extraction method. The integrity of the liposomes was confirmed by performing cryo-electron microscopy (cryo-EM) analysis of the liposomes and syndesomes (FIG. 2). To create a local delivery platform for release of the syndesomes into the wound, the compounds were encapsulated into alginate disks using a custom made mold to generate 6 mm alginate disks (FIG. 4). The disks were lyophilized to be imaged under the SEM to check for surface properties (FIG. 3).

Figures 5A, 5B:
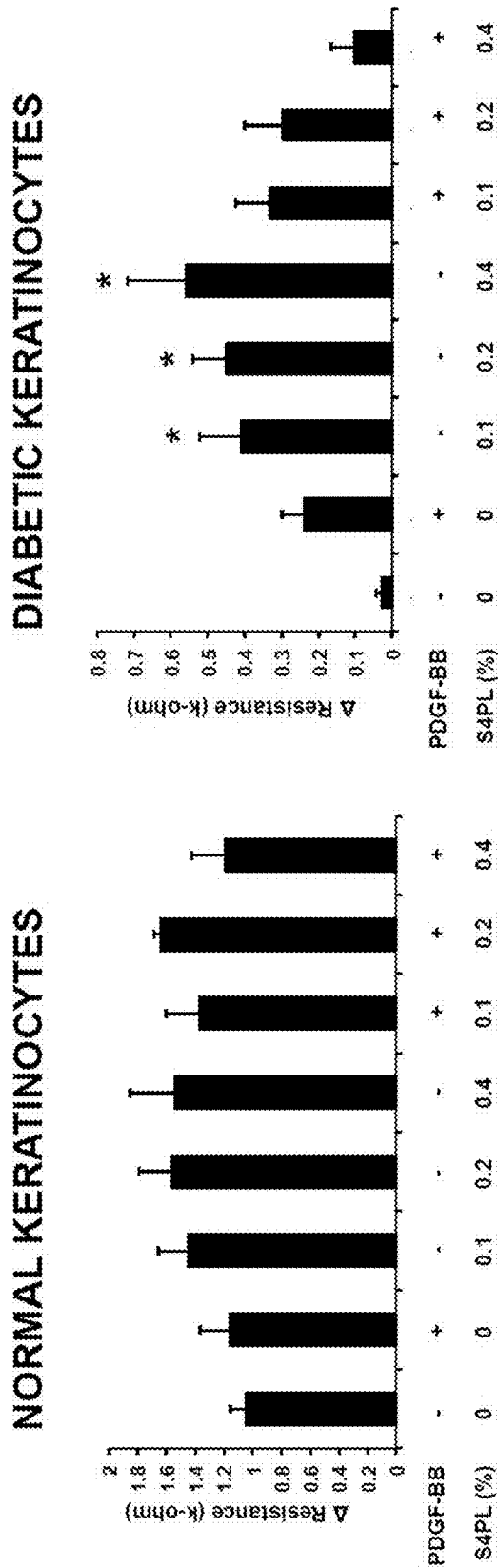
FIGS. 5A and 5B are bar graphs showing ECIS migration (resistance change, k-ohm) of normal keratinocytes (FIG. 5A) and diabetic keratinocytes (FIG. 5B) treated with syndesomes (S4PL) (0-0.4%) with and without PDGF-BB. *P<0.05.
Figure 6:
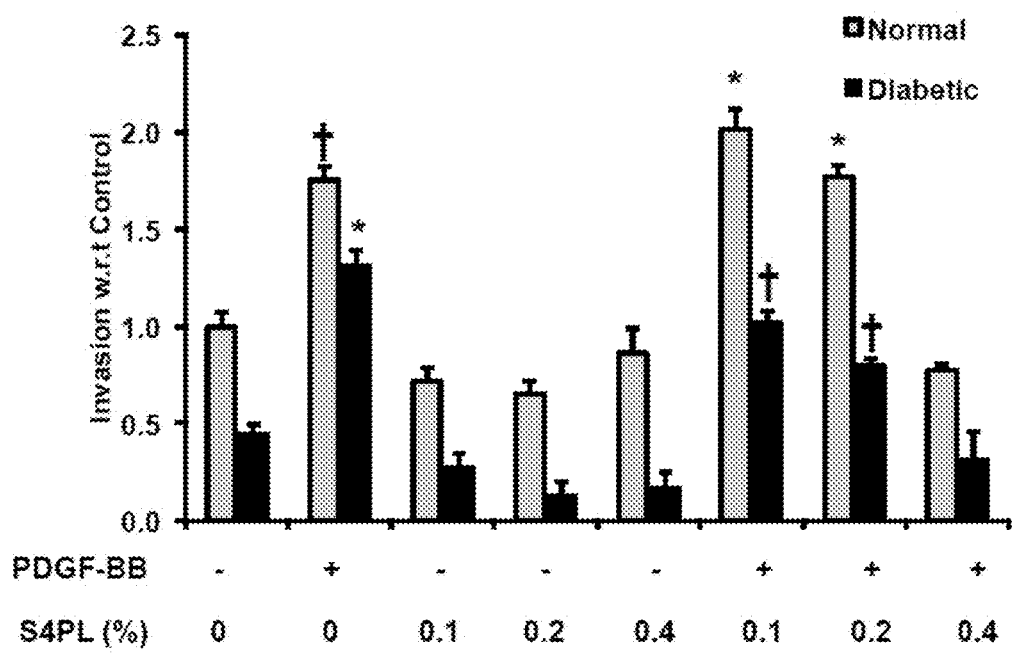
FIG. 6 is a bar graph showing invasion of normal (grey bars) and diabetic keratinocytes (black bars) treated with syndesomes (S4PL) (0-0.4%) with and without PDGF-BB. † wrt SP4PL. * wrt control and S4PL.
Figure 7:
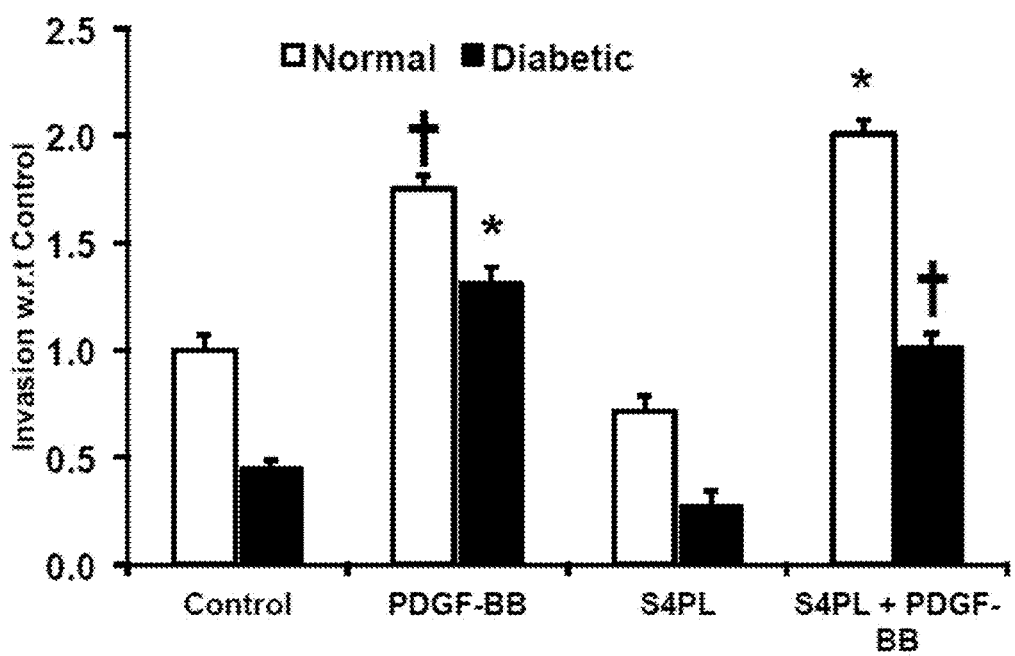
FIG. 7 is a bar graph showing invasion of normal (white bars) and diabetic keratinocytes (black bars) treated with control, PDGF-BB, 0.1% S4PL, or PDGF-BB and 0.1% S4PL. † wrt SP4PL. *wrt control and S4PL.

Syndesomes enhance keratinocyte migration, and reduce fibroblast invasion. Next assessed was whether exogenous delivery of syndecan-4 could enhance the migration of epidermal keratinocytes and invasion of dermal fibroblasts, two key cellular effectors of wound healing. Keratinocytes from non-diabetic donors showed only a moderate increase in migration in the groups treated with both syndecan-4 and PDGF-BB (FIG. 5A). Keratinocytes from diabetic patients showed a nearly two-fold increase in migration with treatment with the syndecan-4 proteoliposomes at the optimal concentration (0.4% S4PL; FIG. 5B). Surprisingly, the syndesomes alone were more effective at inducing migration than in combination with PDGF-BB. Higher doses of syndecan-4 with PDGF-BB demonstrated a reduction in migration for both cell lines. The invasion of fibroblasts was also measured through a collagen-I gel under various treatment conditions. A moderate increase in migration with syndesome treatment in non-diabetic fibroblasts and decrease compared to PDGF-BB group in the diabetic fibroblasts was observed (FIG. 6, 7).

Figure 8:
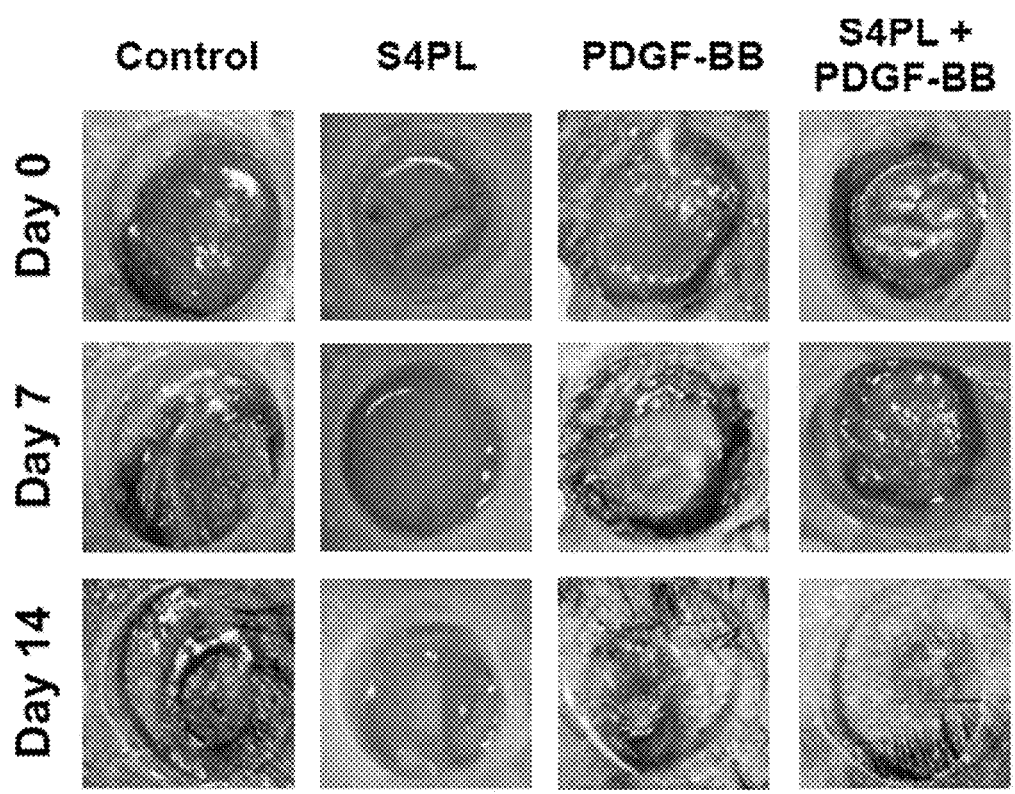
FIG. 8 is an image showing wound healing after 0, 7, and 14 days of treatment with control, 0.1% S4PL, PDGF-BB, or PDGF-BB and S4PL.
Figure 9:
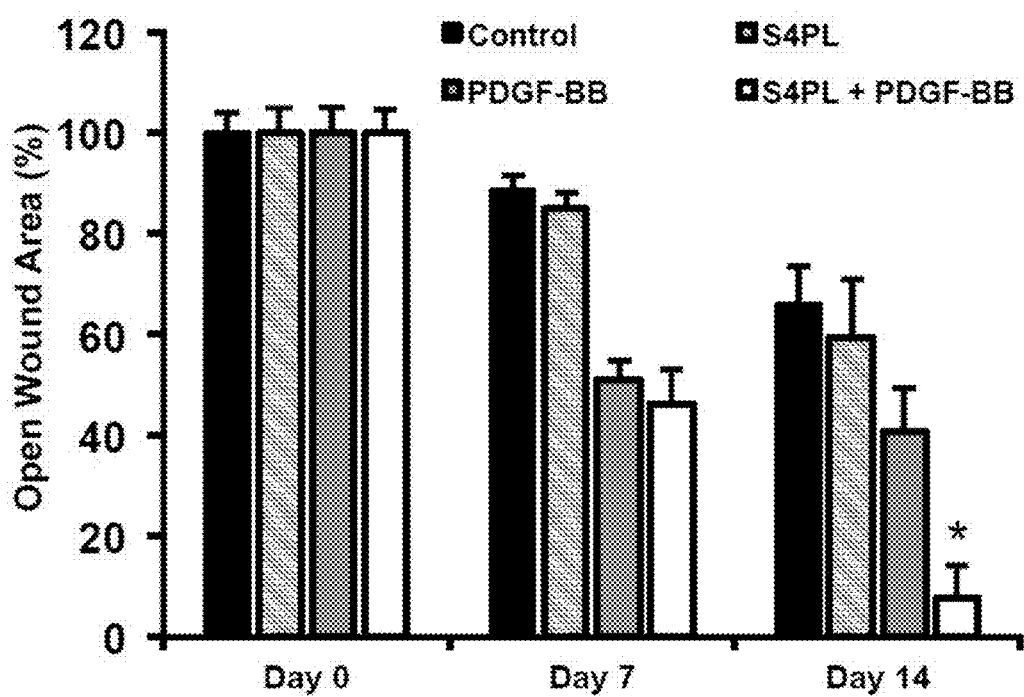
FIG. 9 is a bar graph showing open wound area (%) at 0, 7, and 14 days after treatment with control (black bars), PDGF-BB (gray bars), S4PL (hatched bars), or PDGF-BB and S4PL (white bars).
Figure 10:
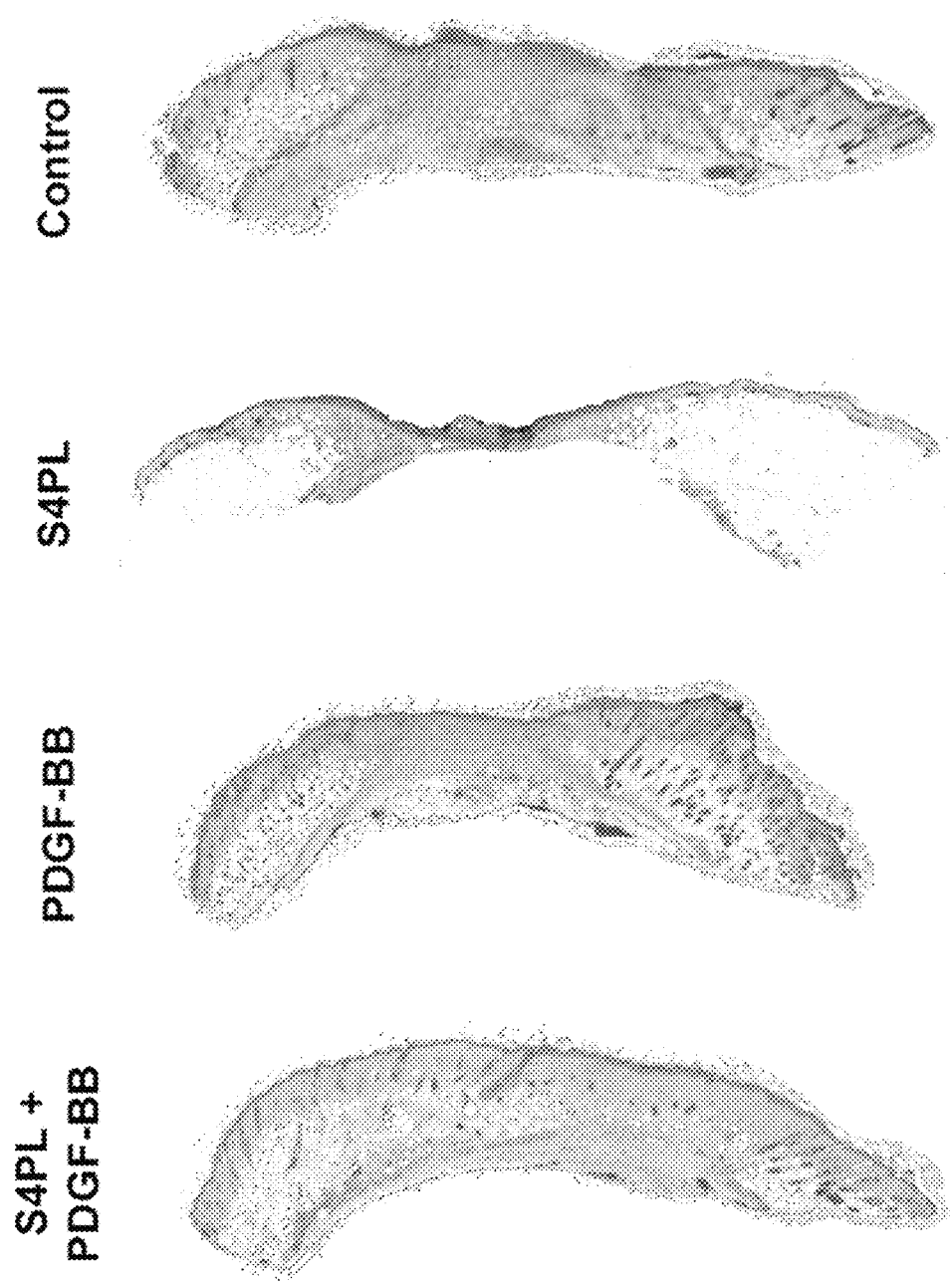
FIG. 10 is an image Hematoxylin and Eosin stained sections of the cutaneous wounds in mice treated with control, PDGF-BB, S4PL, or PDGF-BB and S4PL.
Figure 11A:
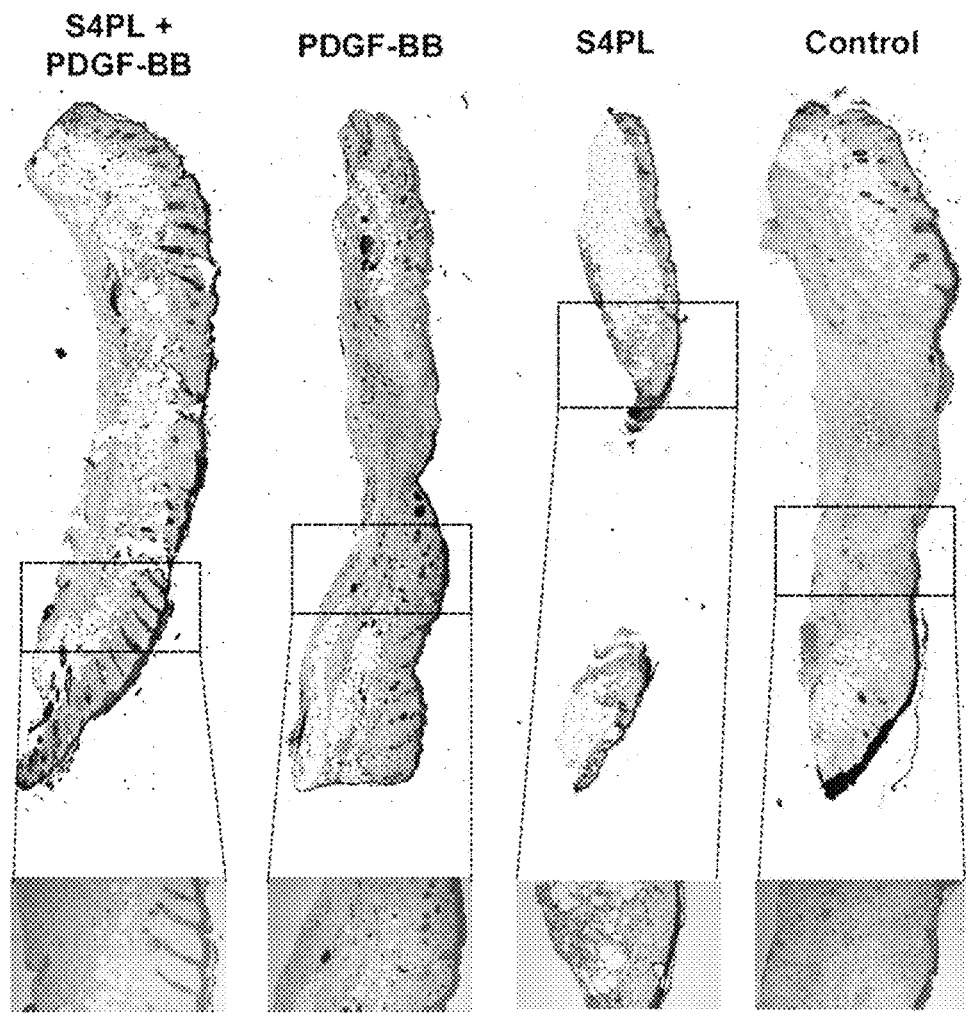
FIGS. 11A and 11B are images (FIG. 11A) and bar graph (FIG. 11B) showing epidermal re-growth (mm) in skin wounds treated with control, PDGF-BB, S4PL, or PDGF-BB and S4PL.
Figure 11B:
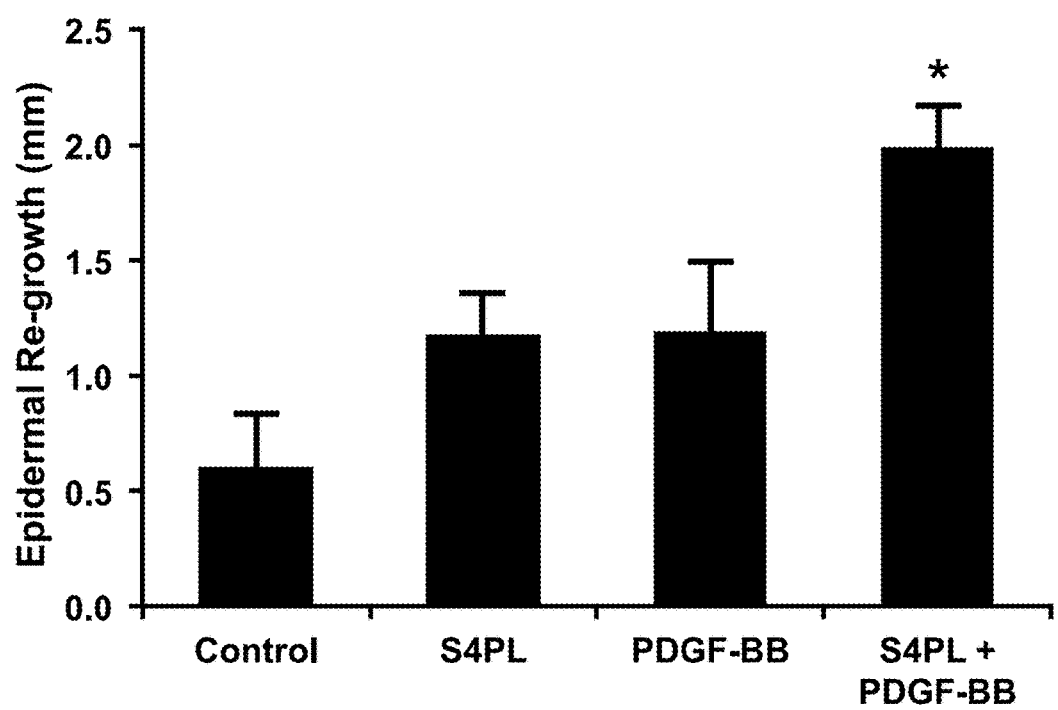

Syndesomes improve wound healing in obese, diabetic mice. The effectiveness of syndesome therapy for enhancing wound healing was next tested in the diabetic ob/ob mouse model. Full-thickness wounds ere created on the dorsal surface of these mice and a silicone splint attached around the wound using glue and sutures to prevent contraction. Alginate wound dressings that matched the size of the wounds were created using a custom-designed mold (FIG. 4). The gels were replaced seven days after the initial wounding and the mice were allowed to heal for an additional seven days. A macroscopic analysis of wound closure revealed a two-fold decrease in wound size after 14 days in the syndesomes with PDGF-BB treatment compared to PDGF-BB alone (FIG. 8, 9). A histological analysis of the wound beds demonstrated increased cellular infiltration in the syndesome with PDGF-BB group in comparison to the other groups including the syndesomes alone (FIG. 10). Immunostaining was performed for cytokeratin and the regeneration of the epidermis beyond the initial wound defect was measured. A morphometric quantification showed increase re-epithelization in the syndesome with PDGF-BB group over the other treatment groups (FIG. 11A, 11B).

Figure 12A:
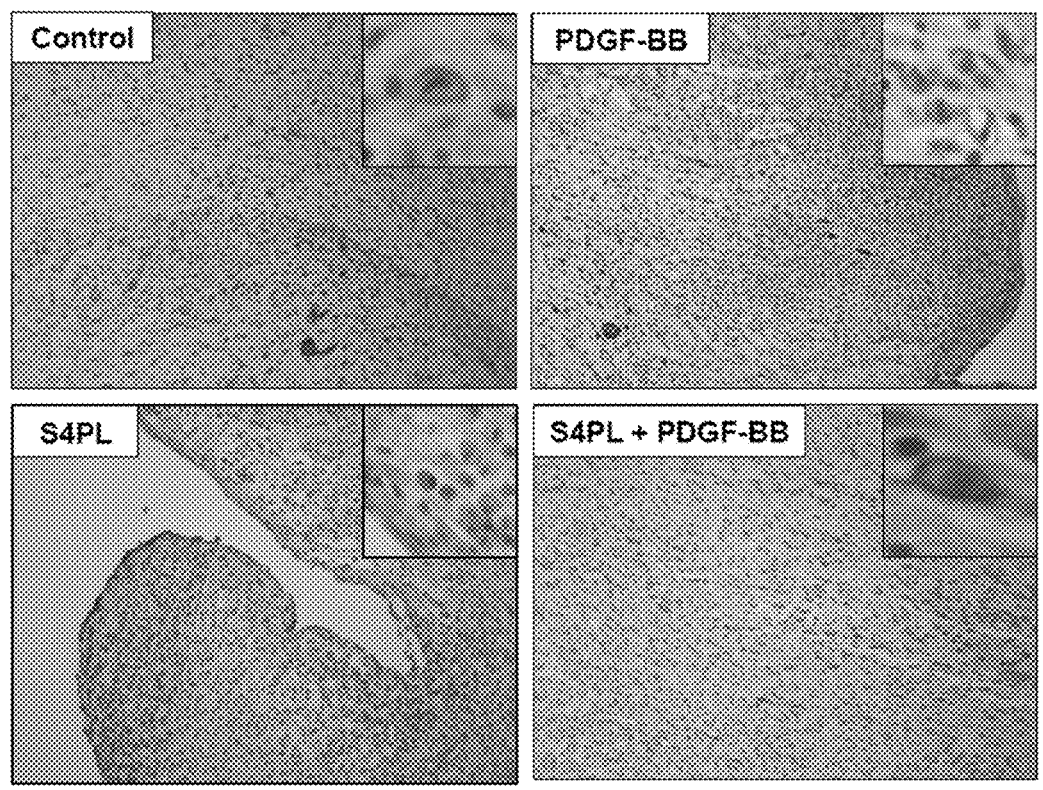
FIGS. 12A and 12B are images (FIG. 12A) and bar graph (FIG. 12B) showing M1 macrophage marker—CD86 positive cells (%) in skin wounds treated with control, PDGF-BB, S4PL, or PDGF-BB and S4PL.
Figure 12B:
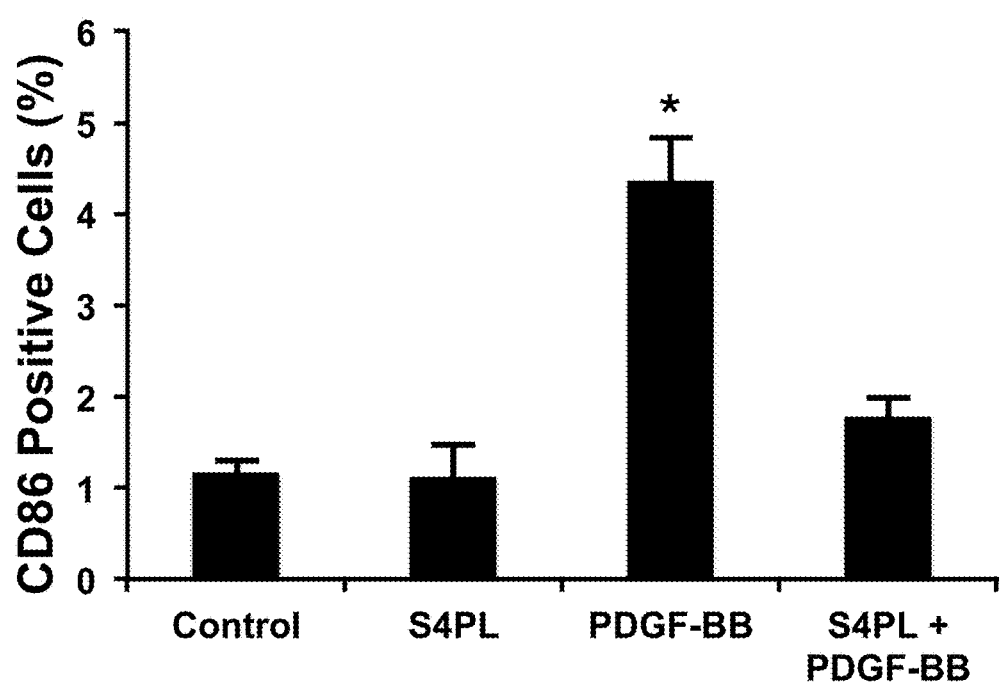
Figure 13A:
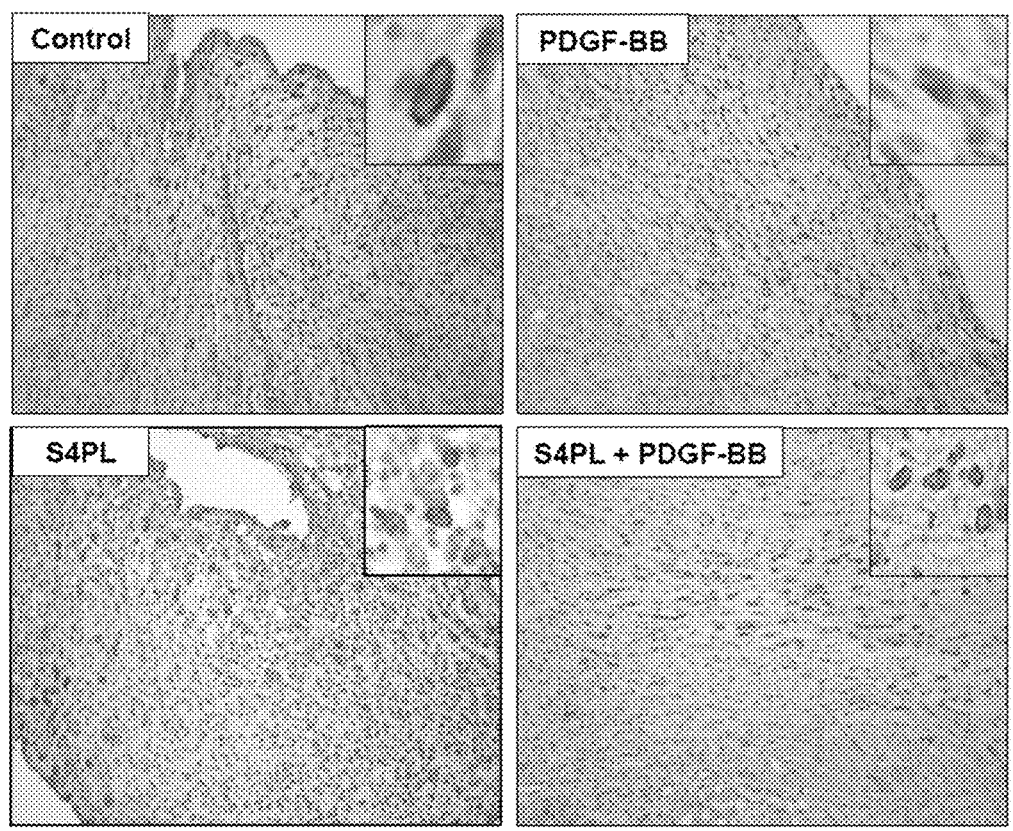
FIGS. 13A and 13B are images (FIG. 13A) and bar graph (FIG. 13B) showing M2 macrophage marker—CD163 positive cells (%) in skin wounds treated with control, PDGF-BB, S4PL, or PDGF-BB and S4PL.
Figure 13B:
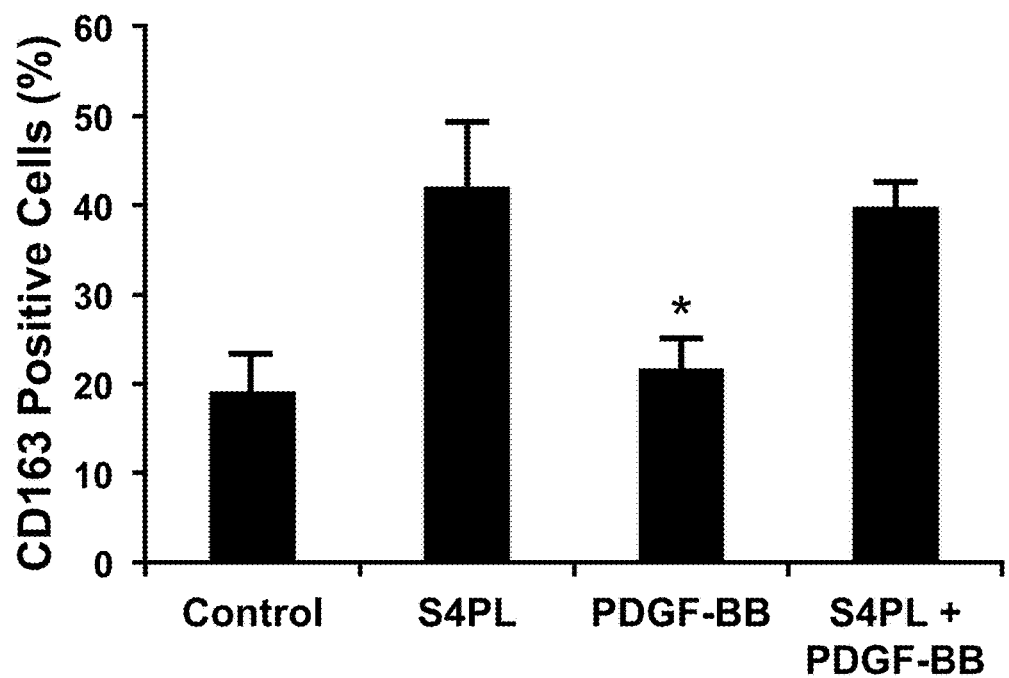
Figure 14A:
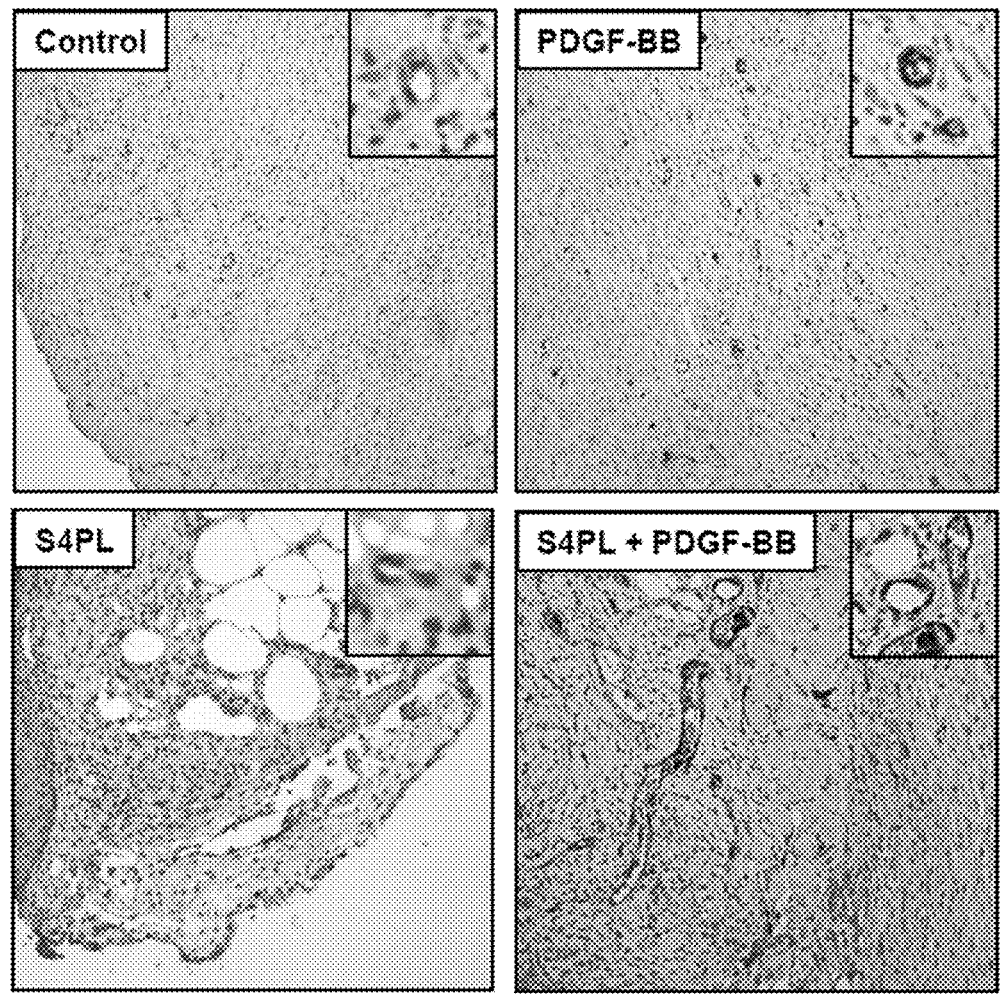
FIG. 14A contains images of skin wounds treated with control, PDGF-BB, S4PL, or PDGF-BB and S4PL, and stained for blood vessels.
Figure 14B:
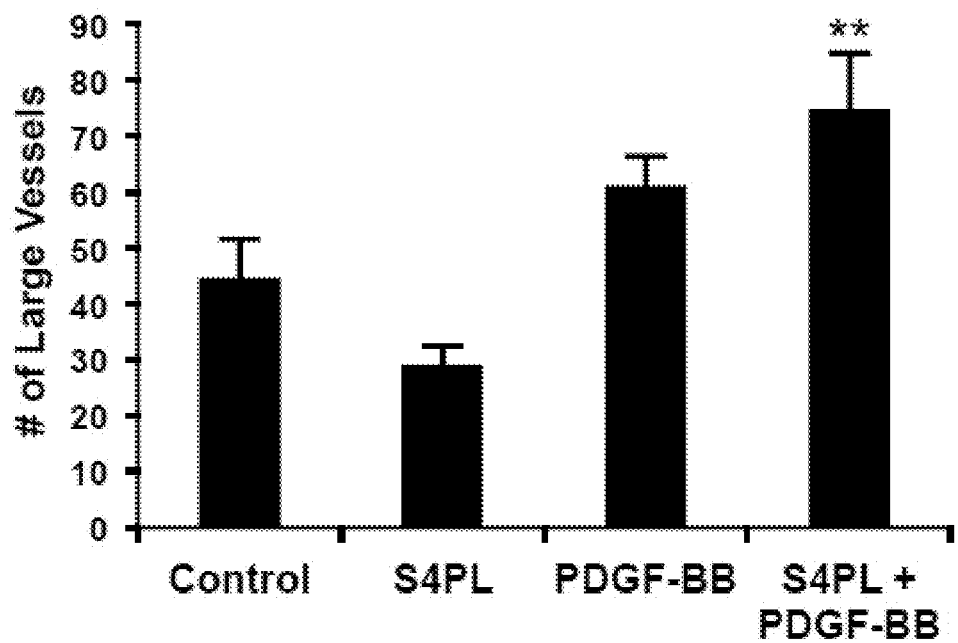
FIGS. 14B and 14C are bar graphs showing the number of large vessels (FIG. 14B) and small vessels (FIG. 14C) in these skin wounds.
Figure 14C:
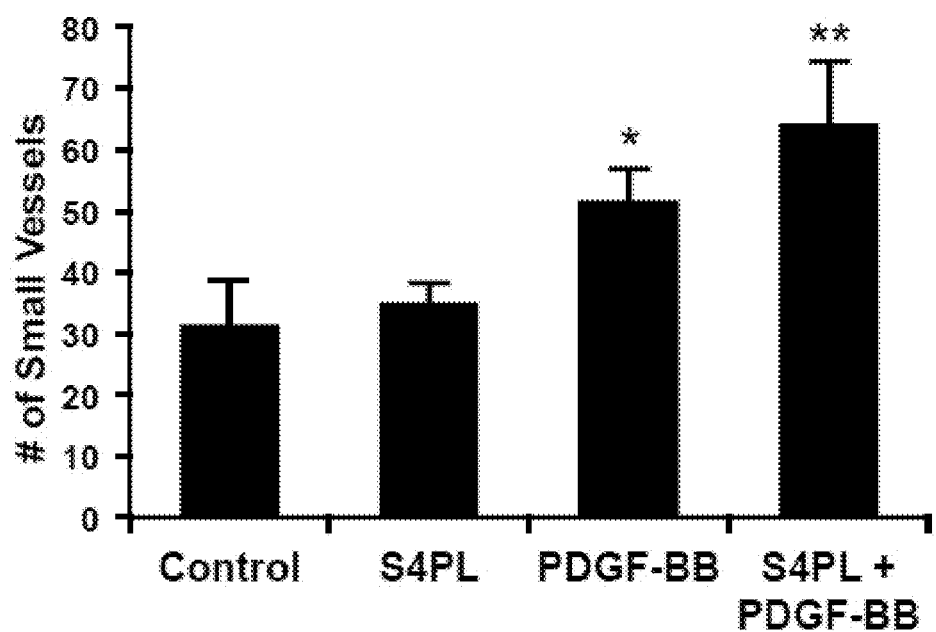

Syndesomes enhance angiogenesis in the wound and increase wound healing phenotype in macrophages. Macrophages are key players in the wound healing cascade through the regulation of inflammation and healing responses. Macrophages can express a continuum of phenotypes that are often broadly classified into M1 macrophages with pro-inflammatory activities or M2 macrophages that orchestrate matrix deposition and wound healing. The expression of CD86 (M1 marker) and CD163 (M2 marker) was examined using immunostaining of histological sections from the mice treated with syndesome-incorporating alginate wound dressings after 14 days. This analysis demonstrated a decrease in the expression of CD86 with syndesome treatment (FIG. 12A, 12B). In addition, the levels of the M2 marker CD163 were increased in the wound beds (FIG. 13A, 13B). Interestingly, the modulation of the marker expression was present in both the syndesomes with PDGF-BB and in the S4PL alone groups, suggesting that the syndesomes were directly inducing immunomodulation in the wounds. The wound beds were harvested and immunostaining for endothelial cells was performed (von Willebrand factor). This analysis showed increased blood vessels in the wound bed of the PDGF-BB with syndesome treated group in comparison to all other groups (FIG. 14A). Quantification of number of large and small vessels showed significantly higher number in the S4PL with PDGF-BB group compared to all groups (FIG. 14B, 14C).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A composition comprising: a) a proteovesicle comprising a syndecan-4 polypeptide embedded in a lipid vesicle, and b) a growth factor polypeptide, wherein the growth factor polypeptide is platelet derived growth factor BB (PDGF-BB).

2. The composition of claim 1, wherein the composition further comprises a PDGF receptor embedded in the lipid vesicle.

3. The composition of claim 2, wherein the PDGF receptor binds to PDGF-BB.

4. The composition of claim 2, wherein the PDGF receptor is PDGFRα, PDGFRβ, or combinations, or heterodimers thereof.

5. The composition of claim 1, wherein the PDGF-BB polypeptide and the proteovesicle are encapsulated in a biodegradable microbead.

6. The composition of claim 5, wherein the microbead comprises a biocompatible hydrogel.

7. The composition of claim 6, wherein the biocompatible hydrogel comprises a polysaccharide.

8. The composition of claim 7, wherein the biocompatible hydrogel comprises alginate.

9. The composition of claim 5, wherein the microbead is from 1 μm in diameter up to 3 μm in diameter.

10. The composition of claim 1, wherein the composition further comprises a wound dressing.

11. The composition of claim 1, wherein the PDGF-BB polypeptide and the proteovesicle are encapsulated in a biodegradable microcapsule.

12. A method for enhancing wound healing in a subject, comprising administering to a subject in need thereof therapeutically effective amounts of (a) a proteovesicle comprising a syndecan-4 polypeptide embedded in a lipid vesicle and (b) a growth factor polypeptide, wherein the growth factor polypeptide is PDGF-BB.

13. The method of claim 12, wherein the proteovesicle and the PDGF-BB polypeptide are co-administered to the subject.

14. The method of claim 12, wherein the wound is a chronic wound.

15. The method of claim 12, wherein the wound is a skin wound.

* * * * *

UNITED STATES PATENT AND TRADEMARK OFFICE
CERTIFICATE OF CORRECTION

PATENT NO. : 10,086,041 B2
APPLICATION NO. : 15/387201
DATED : October 2, 2018
INVENTOR(S) : Aaron B. Baker et al.

Page 1 of 1

It is certified that error appears in the above-identified patent and that said Letters Patent is hereby corrected as shown below:

In the Claims

Column 18, Line 46, should read:
"The composition of claim 5, wherein the microbead is from 1 um in diameter up to 3 mm in diameter."

Signed and Sealed this
Eighteenth Day of June, 2019

Andrei Iancu
*Director of the United States Patent and Trademark Office*